(12) United States Patent
Cabiri et al.

(10) Patent No.: US 12,036,394 B2
(45) Date of Patent: Jul. 16, 2024

(54) INJECTOR NEEDLE CAP AND/OR LINER REMOVER

(71) Applicant: West Pharma. Services IL, Ltd., Ra'anana (IL)

(72) Inventors: Oz Cabiri, Macabim-Reut (IL); Ran Hezkiahu, Herzliya (IL)

(73) Assignee: West Pharma. Services IL, Ltd., Ra'anana (IL)

(*) Notice: Subject to any disclaimer, the term of this patent is extended or adjusted under 35 U.S.C. 154(b) by 30 days.

(21) Appl. No.: 17/696,521

(22) Filed: Mar. 16, 2022

(65) Prior Publication Data
US 2022/0273879 A1    Sep. 1, 2022

Related U.S. Application Data

(60) Division of application No. 15/766,670, filed as application No. PCT/US2016/056247 on Oct. 10, (Continued)

(51) Int. Cl.
*A61M 5/31*    (2006.01)
*A61M 5/142*   (2006.01)
(Continued)

(52) U.S. Cl.
CPC ............ *A61M 5/28* (2013.01); *A61M 5/3134* (2013.01); *A61M 5/3202* (2013.01); *A61M 5/3204* (2013.01); *A61M 5/34* (2013.01); *B29C 33/12* (2013.01); *B65D 1/36* (2013.01); *B65D 5/503* (2013.01); *B65D 21/0233* (2013.01); *B65D 25/108* (2013.01); *A61M 5/14248* (2013.01); *A61M 5/1456* (2013.01); *A61M 2005/1581* (2013.01); *A61M 2005/312* (2013.01); *A61M 2005/341* (2013.01); (Continued)

(58) Field of Classification Search
CPC .... A61M 5/28; A61M 5/3134; A61M 5/3202; A61M 5/3204; A61M 5/14248; A61M 5/1456; A61M 2005/1581
See application file for complete search history.

(56) References Cited

U.S. PATENT DOCUMENTS 232,432 A    9/1880 Allison
1,125,887 A  1/1915 Schimmel
(Continued)

FOREIGN PATENT DOCUMENTS

CN    1071846    5/1993
CN    1118273    3/1996
(Continued)

OTHER PUBLICATIONS

US 8,333,733 B2, 12/2012, Lanigan et al. (withdrawn)
(Continued)

*Primary Examiner* — Tasnim Mehjabin Ahmed
(74) *Attorney, Agent, or Firm* — Blank Rome LLP

(57) ABSTRACT

A system for medicament delivery includes a cartridge containing a medicament and in fluid communication with a needle, where the needle is enveloped by a needle cap, a housing for containing the cartridge and having an orifice for allowing access to said needle cap and its associated needle, and a needle cap remover device.

26 Claims, 19 Drawing Sheets

Related U.S. Application Data 2016, now Pat. No. 11,318,254, which is a continuation of application No. 15/269,248, filed on Sep. 19, 2016, now Pat. No. 10,086,145, and a continuation of application No. 15/204,542, filed on Jul. 7, 2016, now Pat. No. 10,576,207.

(60) Provisional application No. 62/281,536, filed on Jan. 21, 2016, provisional application No. 62/284,806, filed on Oct. 9, 2015.

(51) Int. Cl.

| | | |
|---|---|---|
| *A61M 5/158* | (2006.01) | |
| *A61M 5/28* | (2006.01) | |
| *A61M 5/32* | (2006.01) | |
| *A61M 5/34* | (2006.01) | |
| *B29C 33/12* | (2006.01) | |
| *B65D 1/36* | (2006.01) | |
| *B65D 5/50* | (2006.01) | |
| *B65D 21/02* | (2006.01) | |
| *B65D 25/10* | (2006.01) | |
| *A61M 5/145* | (2006.01) | |
| *B29L 31/00* | (2006.01) | |

(52) U.S. Cl.
CPC . *A61M 2205/3306* (2013.01); *A61M 2207/00* (2013.01); *B29L 2031/7544* (2013.01)

(56) References Cited

U.S. PATENT DOCUMENTS

| | | |
|---|---|---|
| 1,321,550 A | 11/1919 | Frank et al. |
| 1,704,921 A | 3/1929 | Nicoll |
| 1,795,530 A | 3/1931 | Cowan et al. |
| 1,795,630 A | 3/1931 | Wilson |
| 2,453,590 A | 11/1948 | Poux |
| 2,589,426 A | 3/1952 | Ogle |
| 2,677,373 A | 5/1954 | George |
| 2,702,547 A | 2/1955 | Glass |
| 2,860,635 A | 11/1958 | Wilburn |
| 3,203,269 A | 8/1965 | Perrine |
| 3,212,685 A | 10/1965 | James et al. |
| 3,585,439 A | 6/1971 | Schneeberger |
| 3,623,474 A | 11/1971 | Heilman et al. |
| 3,705,582 A | 12/1972 | Stumpf et al. |
| 3,708,945 A | 1/1973 | Klettke |
| 3,794,028 A | 2/1974 | Mueller et al. |
| 3,834,387 A | 9/1974 | Brown |
| 3,994,295 A | 11/1976 | Wulff |
| 4,085,747 A | 4/1978 | Lee |
| 4,189,065 A | 2/1980 | Herold |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,324,262 A | 4/1982 | Hall |
| 4,403,987 A | 9/1983 | Gottinger |
| 4,425,120 A | 1/1984 | Sampson et al. |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,549,554 A | 10/1985 | Markham |
| 4,564,054 A | 1/1986 | Gustavsson |
| 4,565,543 A | 1/1986 | Bekkering et al. |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,636,201 A | 1/1987 | Ambrose et al. |
| 4,664,654 A | 5/1987 | Strauss |
| 4,685,903 A | 8/1987 | Cable et al. |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan et al. |
| 4,710,178 A | 12/1987 | Henri et al. |
| 4,729,208 A | 3/1988 | Galy et al. |
| 4,735,311 A | 4/1988 | Lowe et al. |
| 4,737,144 A | 4/1988 | Choksi |
| 4,772,272 A | 9/1988 | Mcfarland |
| 4,810,215 A | 3/1989 | Kaneko |
| 4,810,249 A | 3/1989 | Haber et al. |
| 4,813,426 A | 3/1989 | Haber et al. |
| 4,840,185 A | 6/1989 | Hernandez |
| 4,850,966 A | 7/1989 | Grau et al. |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | Mcnaughton |
| 4,882,575 A | 11/1989 | Kawahara |
| 4,886,499 A | 12/1989 | Cirelli et al. |
| 4,892,521 A | 1/1990 | Laico et al. |
| 4,897,083 A | 1/1990 | Martell |
| 4,900,310 A | 2/1990 | Ogle, II |
| 4,915,702 A | 4/1990 | Haber |
| 4,919,569 A | 4/1990 | Wittenzellner |
| 4,919,596 A | 4/1990 | Slate et al. |
| 4,923,446 A | 5/1990 | Page et al. |
| 4,929,241 A | 5/1990 | Kulli |
| 4,950,241 A | 8/1990 | Ranford |
| 4,950,246 A | 8/1990 | Muller |
| 4,957,490 A | 9/1990 | Byrne et al. |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn et al. |
| 5,109,850 A | 5/1992 | Blanco et al. |
| 5,112,317 A | 5/1992 | Michel |
| 5,114,406 A | 5/1992 | Gabriel et al. |
| 5,127,910 A | 7/1992 | Talonn et al. |
| 5,131,816 A | 7/1992 | Brown et al. |
| 5,147,326 A | 9/1992 | Talonn et al. |
| 5,156,599 A | 10/1992 | Ranford et al. |
| 5,190,521 A | 3/1993 | Hubbard et al. |
| 5,217,437 A | 6/1993 | Talonn et al. |
| 5,246,670 A | 9/1993 | Haber et al. |
| 5,254,096 A | 10/1993 | Rondelet et al. |
| 5,267,977 A | 12/1993 | Feeney, Jr. |
| 5,269,762 A | 12/1993 | Armbruster et al. |
| 5,275,582 A | 1/1994 | Wimmer |
| 5,282,593 A | 2/1994 | Fast |
| 5,295,966 A | 3/1994 | Stern et al. |
| 5,298,023 A | 3/1994 | Haber et al. |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell et al. |
| 5,348,544 A | 9/1994 | Sweeney et al. |
| 5,366,498 A | 11/1994 | Brannan et al. |
| 5,376,785 A | 12/1994 | Chin et al. |
| 5,383,865 A | 1/1995 | Michel |
| D356,150 S | 3/1995 | Duggan et al. |
| 5,415,645 A | 5/1995 | Friend et al. |
| 5,456,360 A | 10/1995 | Griffin |
| 5,478,315 A | 12/1995 | Brothers et al. |
| 5,478,316 A | 12/1995 | Bitdinger et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,624 A | 10/1996 | Righi et al. |
| 5,562,686 A | 10/1996 | Sauer et al. |
| 5,593,390 A | 1/1997 | Castellano et al. |
| 5,609,580 A | 3/1997 | Kwiatkowski et al. |
| 5,611,785 A | 3/1997 | Mito et al. |
| 5,616,132 A | 4/1997 | Newman |

(56) References Cited

U.S. PATENT DOCUMENTS

| | | |
|---|---|---|
| 5,624,400 A | 4/1997 | Firth et al. |
| 5,637,095 A | 6/1997 | Nason et al. |
| 5,643,218 A | 7/1997 | Lynn et al. |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Oesterlind et al. |
| 5,690,618 A | 11/1997 | Smith et al. |
| 5,697,908 A | 12/1997 | Imbert et al. |
| 5,697,916 A | 12/1997 | Schraga |
| 5,725,500 A | 3/1998 | Micheler |
| 5,728,075 A | 3/1998 | Levander |
| D393,314 S | 4/1998 | Meisner et al. |
| 5,741,275 A | 4/1998 | Wyssmann |
| 5,766,186 A | 6/1998 | Faraz et al. |
| 5,776,103 A | 7/1998 | Kriesel et al. |
| 5,795,675 A | 8/1998 | Maglica |
| 5,800,420 A | 9/1998 | Gross et al. |
| 5,807,375 A | 9/1998 | Gross et al. |
| 5,810,167 A | 9/1998 | Fujii |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,931,814 A | 8/1999 | Alex et al. |
| 5,941,850 A | 8/1999 | Shah et al. |
| 5,944,699 A | 8/1999 | Barrelle et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,989,221 A | 11/1999 | Hjertman |
| 5,993,423 A | 11/1999 | Choi |
| 6,004,296 A | 12/1999 | Jansen et al. |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,045,533 A | 4/2000 | Kriesel et al. |
| 6,064,797 A | 5/2000 | Crittendon et al. |
| 6,074,369 A | 6/2000 | Sage et al. |
| 6,162,197 A | 12/2000 | Mohammad |
| 6,186,979 B1 | 2/2001 | Dysarz |
| 6,186,982 B1 | 2/2001 | Gross et al. |
| 6,189,292 B1 | 2/2001 | Odell et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,270,481 B1 | 8/2001 | Mason et al. |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,362,591 B1 | 3/2002 | Moberg |
| 6,377,848 B1 | 4/2002 | Garde et al. |
| 6,391,005 B1 | 5/2002 | Lum et al. |
| 6,423,029 B1 | 7/2002 | Elsberry |
| D461,243 S | 8/2002 | Niedospial |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,554,800 B1 | 4/2003 | Nezhadian et al. |
| 6,555,986 B2 | 4/2003 | Moberg |
| 6,558,351 B1 | 5/2003 | Steil et al. |
| 6,565,541 B2 | 5/2003 | Sharp |
| 6,585,695 B1 | 7/2003 | Adair et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,685,678 B2 | 2/2004 | Evans et al. |
| 6,689,118 B2 | 2/2004 | Alchas et al. |
| 6,699,218 B2 | 3/2004 | Flaherty et al. |
| 6,719,141 B2 | 4/2004 | Heinz et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,783 B2 | 6/2004 | Hung et al. |
| 6,752,787 B1 | 6/2004 | Causey et al. |
| 6,767,336 B1 | 7/2004 | Kaplan |
| 6,768,425 B2 | 7/2004 | Flaherty et al. |
| 6,786,890 B2 | 9/2004 | Preuthun et al. |
| 6,800,071 B1 | 10/2004 | Mcconnell et al. |
| 6,805,687 B2 | 10/2004 | Dextradeur et al. |
| 6,817,990 B2 | 11/2004 | Yap et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,907,679 B2 | 6/2005 | Yarborough et al. |
| 6,908,452 B2 | 6/2005 | Diaz et al. |
| 6,960,192 B1 | 11/2005 | Flaherty et al. |
| 6,979,316 B1 | 12/2005 | Rubin et al. |
| 6,997,727 B1 | 2/2006 | Legrady et al. |
| 7,001,360 B2 | 2/2006 | Veasey et al. |
| 7,004,104 B1 | 2/2006 | Kundus |
| 7,004,929 B2 | 2/2006 | McWethy et al. |
| 7,025,226 B2 | 4/2006 | Ramey |
| 7,033,338 B2 | 4/2006 | Vilks et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,063,684 B2 | 6/2006 | Moberg |
| 7,066,909 B1 | 6/2006 | Peter et al. |
| 7,094,221 B2 | 8/2006 | Veasey et al. |
| 7,097,637 B2 | 8/2006 | Triplett et al. |
| 7,112,187 B2 | 9/2006 | Karlsson |
| 7,128,727 B2 | 10/2006 | Flaherty et al. |
| 7,144,384 B2 | 12/2006 | Gorman et al. |
| 7,193,521 B2 | 3/2007 | Moberg et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| RE39,923 E | 11/2007 | Blom |
| 7,291,132 B2 | 11/2007 | Deruntz et al. |
| 7,291,159 B2 | 11/2007 | Schmelzeisen-Redeker et al. |
| 7,303,549 B2 | 12/2007 | Flaherty et al. |
| 7,306,578 B2 | 12/2007 | Gray et al. |
| 7,326,194 B2 | 2/2008 | Zinger et al. |
| 7,344,385 B2 | 3/2008 | Chen |
| 7,364,570 B2 | 4/2008 | Gerondale et al. |
| 7,377,912 B2 | 5/2008 | Graf et al. |
| 7,390,312 B2 | 6/2008 | Barrelle |

(56) References Cited

U.S. PATENT DOCUMENTS

| | | |
|---|---|---|
| 7,390,314 B2 | 6/2008 | Stutz et al. |
| 7,407,493 B2 | 8/2008 | Cane |
| 7,418,880 B1 | 9/2008 | Smith |
| D578,210 S | 10/2008 | Muta et al. |
| 7,442,186 B2 | 10/2008 | Blomquist |
| 7,455,663 B2 | 11/2008 | Bikovsky |
| 7,465,290 B2 | 12/2008 | Reilly |
| 7,468,055 B2 | 12/2008 | Prais et al. |
| 7,488,181 B2 | 2/2009 | Van |
| 7,497,842 B2 | 3/2009 | Diaz et al. |
| 7,500,963 B2 | 3/2009 | Westbye et al. |
| 7,501,587 B2 | 3/2009 | English |
| 7,503,786 B2 | 3/2009 | Kato et al. |
| 7,530,964 B2 | 5/2009 | Lavi et al. |
| 7,540,858 B2 | 6/2009 | Dibiasi |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| 7,597,682 B2 | 10/2009 | Moberg |
| D604,835 S | 11/2009 | Conley |
| 7,611,491 B2 | 11/2009 | Pickhard |
| 7,621,893 B2 | 11/2009 | Moberg et al. |
| 7,628,770 B2 | 12/2009 | Ethelfeld |
| 7,628,772 B2 | 12/2009 | Mcconnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,658,734 B2 | 2/2010 | Adair et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,333 B2 | 6/2010 | Gillespie, III |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,758,548 B2 | 7/2010 | Gillespie et al. |
| 7,758,550 B2 | 7/2010 | Bollenbach et al. |
| 7,766,867 B2 | 8/2010 | Lynch et al. |
| 7,766,873 B2 | 8/2010 | Moberg et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,801,599 B2 | 9/2010 | Young et al. |
| 7,806,868 B2 | 10/2010 | De et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,854,723 B2 | 12/2010 | Wang et al. |
| 7,857,131 B2 | 12/2010 | Vedrine |
| 7,879,025 B2 | 2/2011 | Jacobson et al. |
| 7,892,206 B2 | 2/2011 | Moberg et al. |
| 7,901,382 B2 | 3/2011 | Daily et al. |
| 7,905,867 B2 | 3/2011 | Veasey et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,976,514 B2 | 7/2011 | Abry et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 7,998,131 B2 | 8/2011 | Adair et al. |
| 8,002,754 B2 | 8/2011 | Kawamura et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,034,026 B2 | 10/2011 | Grant et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,255 B2 | 11/2011 | Brunnberg et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| 8,118,781 B2 | 2/2012 | Knopper et al. |
| 8,121,603 B2 | 2/2012 | Zhi |
| D657,462 S | 4/2012 | Siroky |
| 8,147,446 B2 | 4/2012 | Yodfat et al. |
| 8,151,169 B2 | 4/2012 | Bieth et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,257,345 B2 | 9/2012 | Adair et al. |
| 8,267,893 B2 | 9/2012 | Moberg et al. |
| 8,267,921 B2 | 9/2012 | Yodfat et al. |
| 8,273,061 B2 | 9/2012 | McConnell et al. |
| 8,287,520 B2 | 10/2012 | Drew et al. |
| 8,292,647 B1 | 10/2012 | Mcgrath et al. |
| 8,303,572 B2 | 11/2012 | Adair et al. |
| 8,308,679 B2 | 11/2012 | Hanson et al. |
| 8,308,695 B2 | 11/2012 | Laiosa |
| 8,323,250 B2 | 12/2012 | Chong et al. |
| 8,348,898 B2 | 1/2013 | Cabiri |
| 8,366,668 B2 | 2/2013 | Maritan |
| 8,372,039 B2 | 2/2013 | Mernoe et al. |
| 8,373,421 B2 | 2/2013 | Lindegger et al. |
| 8,409,141 B2 | 4/2013 | Johansen et al. |
| 8,409,142 B2 | 4/2013 | Causey et al. |
| 8,409,143 B2 | 4/2013 | Lanigan et al. |
| 8,409,149 B2 | 4/2013 | Hommann et al. |
| 8,414,533 B2 | 4/2013 | Alexandersson |
| 8,414,557 B2 | 4/2013 | Istoc et al. |

(56) References Cited

U.S. PATENT DOCUMENTS

| | | |
|---|---|---|
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,490,790 B2 | 7/2013 | Cocheteux et al. |
| 8,495,918 B2 | 7/2013 | Bazargan et al. |
| 8,496,862 B2 | 7/2013 | Zelkovich et al. |
| 8,500,716 B2 | 8/2013 | Adair et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,517,992 B2 | 8/2013 | Jones |
| 8,523,803 B1 | 9/2013 | Favreau |
| 8,551,046 B2 | 10/2013 | Causey et al. |
| 8,556,856 B2 | 10/2013 | Bazargan et al. |
| 8,562,364 B2 | 10/2013 | Lin et al. |
| 8,568,361 B2 | 10/2013 | Yodfat et al. |
| 8,574,216 B2 | 11/2013 | Istoc et al. |
| 8,603,026 B2 | 12/2013 | Favreau |
| 8,603,027 B2 | 12/2013 | Favreau |
| 8,603,028 B2 | 12/2013 | Mudd et al. |
| 8,617,110 B2 | 12/2013 | Moberg et al. |
| 8,622,966 B2 | 1/2014 | Causey et al. |
| 8,628,510 B2 | 1/2014 | Bazargan et al. |
| 8,632,499 B2 | 1/2014 | Grant et al. |
| 8,647,074 B2 | 2/2014 | Moberg et al. |
| 8,647,296 B2 | 2/2014 | Moberg et al. |
| 8,647,303 B2 | 2/2014 | Cowe |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| D702,834 S | 4/2014 | Norton et al. |
| 8,690,855 B2 | 4/2014 | Alderete et al. |
| 8,708,961 B2 | 4/2014 | Field et al. |
| 8,715,237 B2 | 5/2014 | Moberg et al. |
| 8,721,603 B2 | 5/2014 | Lundquist |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,784,378 B2 | 7/2014 | Weinandy |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,845,587 B2 | 9/2014 | Lanigan et al. |
| 8,858,508 B2 | 10/2014 | Lavi et al. |
| 8,864,739 B2 | 10/2014 | Moberg et al. |
| 8,876,770 B2 | 11/2014 | Kraft et al. |
| 8,876,778 B2 | 11/2014 | Carrel |
| 8,911,410 B2 | 12/2014 | Ekman et al. |
| 8,915,882 B2 | 12/2014 | Cabiri |
| 8,915,886 B2 | 12/2014 | Cowe |
| 8,920,374 B2 | 12/2014 | Bokelman et al. |
| 8,932,266 B2 | 1/2015 | Wozencroft |
| 8,979,802 B2 | 3/2015 | Woehr |
| 8,986,250 B2 | 3/2015 | Beebe et al. |
| 9,011,164 B2 | 4/2015 | Filman et al. |
| 9,011,371 B2 | 4/2015 | Moberg et al. |
| 9,011,387 B2 | 4/2015 | Ekman et al. |
| 9,033,925 B2 | 5/2015 | Moberg et al. |
| 9,061,104 B2 | 6/2015 | Daniel |
| 9,061,110 B2 | 6/2015 | Avery et al. |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,107,999 B2 | 8/2015 | Moberg et al. |
| 9,138,534 B2 | 9/2015 | Yodfat et al. |
| 9,149,575 B2 | 10/2015 | Cabiri |
| 9,173,996 B2 | 11/2015 | Gray et al. |
| 9,173,997 B2 | 11/2015 | Gross et al. |
| 9,180,248 B2 | 11/2015 | Moberg et al. |
| 9,205,188 B2 | 12/2015 | Lanigan et al. |
| 9,205,199 B2 | 12/2015 | Kemp et al. |
| D747,799 S | 1/2016 | Norton et al. |
| 9,233,215 B2 | 1/2016 | Hourmand et al. |
| 9,259,532 B2 | 2/2016 | Cabiri |
| 9,283,327 B2 | 3/2016 | Hourmand et al. |
| 9,308,318 B2 | 4/2016 | Lanigan et al. |
| 9,308,327 B2 | 4/2016 | Marshall et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,339,607 B2 | 5/2016 | Langley et al. |
| 9,345,834 B2 | 5/2016 | Henley et al. |
| 9,345,836 B2 | 5/2016 | Cabiri et al. |
| 9,350,634 B2 | 5/2016 | Fadell |
| 9,352,090 B2 | 5/2016 | Brereton et al. |
| 9,364,606 B2 | 6/2016 | Cindrich et al. |
| 9,364,608 B2 | 6/2016 | Moberg et al. |
| 9,381,300 B2 | 7/2016 | Smith et al. |
| 9,393,365 B2 | 7/2016 | Cabiri |
| 9,421,323 B2 | 8/2016 | Cabiri et al. |
| 9,421,337 B2 | 8/2016 | Kemp et al. |
| 9,427,531 B2 | 8/2016 | Hourmand et al. |
| 9,433,732 B2 | 9/2016 | Moberg et al. |
| 9,433,733 B2 | 9/2016 | Moberg et al. |
| 9,446,188 B2 | 9/2016 | Grant et al. |
| 9,446,196 B2 | 9/2016 | Hourmand et al. |
| 9,452,261 B2 | 9/2016 | Alon |
| 9,463,280 B2 | 10/2016 | Cabiri |
| 9,463,889 B2 | 10/2016 | Schmitz et al. |
| 9,468,720 B2 | 10/2016 | Mudd et al. |
| 9,474,859 B2 | 10/2016 | Ekman et al. |
| 9,492,622 B2 | 11/2016 | Brereton et al. |
| 9,522,234 B2 | 12/2016 | Cabiri |
| 9,539,384 B2 | 1/2017 | Servansky |
| 9,539,388 B2 | 1/2017 | Causey et al. |
| 9,539,757 B2 | 1/2017 | Ramirez et al. |
| 9,572,926 B2 | 2/2017 | Cabiri |
| 9,572,927 B2 | 2/2017 | Bruggemann et al. |
| 9,579,452 B2 | 2/2017 | Adair et al. |
| 9,579,471 B2 | 2/2017 | Carrel et al. |
| 9,610,407 B2 | 4/2017 | Bruggemann et al. |
| 9,656,019 B2 | 5/2017 | Cabiri et al. |
| 9,656,021 B2 | 5/2017 | Brereton et al. |
| 9,656,025 B2 | 5/2017 | Bostrom et al. |
| 9,707,356 B2 | 7/2017 | Hourmand et al. |
| 9,744,306 B2 | 8/2017 | Cowe |
| 9,775,948 B2 | 10/2017 | Bechmann et al. |
| 9,782,545 B2 | 10/2017 | Gross et al. |
| 9,789,247 B2 | 10/2017 | Kamen et al. |
| 9,814,830 B2 | 11/2017 | Mernoe et al. |
| 9,814,839 B2 | 11/2017 | Eaton |
| 9,849,242 B2 | 12/2017 | Henley et al. |
| 9,862,519 B2 | 1/2018 | Deutschle et al. |
| 9,999,722 B2 | 6/2018 | Yodfat et al. |
| 10,010,681 B2 | 7/2018 | Koch et al. |
| 10,076,356 B2 | 9/2018 | Hadvary et al. |
| 10,143,794 B2 | 12/2018 | Lanigan et al. |
| 10,149,943 B2 | 12/2018 | Bar-El et al. |
| D838,367 S | 1/2019 | Norton et al. |
| 10,166,335 B2 | 1/2019 | Reber et al. |
| 10,207,048 B2 | 2/2019 | Gray et al. |
| 10,207,051 B2 | 2/2019 | Cereda et al. |
| 10,227,161 B2 | 3/2019 | Auerbach |
| 10,232,116 B2 | 3/2019 | Ekman et al. |

(56) References Cited

U.S. PATENT DOCUMENTS

| | | |
|---|---|---|
| 10,258,740 B2 | 4/2019 | McLoughlin et al. |
| 10,376,641 B2 | 8/2019 | Hirschel et al. |
| 10,376,647 B2 | 8/2019 | Farris et al. |
| 10,434,262 B2 | 10/2019 | Bendek et al. |
| 10,500,352 B2 | 12/2019 | Grant et al. |
| 10,561,798 B2 | 2/2020 | Holland et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,722,645 B2 | 7/2020 | Kamen et al. |
| 10,729,847 B2 | 8/2020 | Gray et al. |
| 10,758,679 B2 | 9/2020 | Bar-El et al. |
| 10,842,942 B2 | 11/2020 | Iibuchi et al. |
| 11,027,059 B2 | 6/2021 | Niklaus et al. |
| 2001/0005781 A1 | 6/2001 | Bergens et al. |
| 2001/0018937 A1 | 9/2001 | Nemoto |
| 2001/0021820 A1 | 9/2001 | Lynn |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0055718 A1 | 5/2002 | Hunt |
| 2002/0065488 A1 | 5/2002 | Suzuki et al. |
| 2002/0107487 A1 | 8/2002 | Preuthun |
| 2002/0120186 A1 | 8/2002 | Keimel |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2002/0173748 A1 | 11/2002 | McConnell et al. |
| 2002/0173769 A1 | 11/2002 | Gray et al. |
| 2003/0009133 A1 | 1/2003 | Ramey |
| 2003/0014018 A1 | 1/2003 | Giambattista et al. |
| 2003/0050602 A1 | 3/2003 | Pettis et al. |
| 2003/0069518 A1 | 4/2003 | Daley et al. |
| 2003/0125671 A1 | 7/2003 | Aramata et al. |
| 2003/0130618 A1 | 7/2003 | Gray et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0199825 A1 | 10/2003 | Flaherty et al. |
| 2003/0216683 A1 | 11/2003 | Shekalim |
| 2003/0236498 A1 | 12/2003 | Gross et al. |
| 2004/0000818 A1 | 1/2004 | Preuthun et al. |
| 2004/0003493 A1 | 1/2004 | Adair et al. |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0122359 A1 | 6/2004 | Wenz et al. |
| 2004/0122369 A1 | 6/2004 | Schriver et al. |
| 2004/0127857 A1 | 7/2004 | Shemesh et al. |
| 2004/0135078 A1 | 7/2004 | Mandro et al. |
| 2004/0158172 A1 | 8/2004 | Hancock |
| 2004/0158205 A1 | 8/2004 | Savage |
| 2004/0186419 A1 | 9/2004 | Cho |
| 2004/0186441 A1 | 9/2004 | Graf et al. |
| 2004/0210196 A1 | 10/2004 | Bush et al. |
| 2004/0260233 A1 | 12/2004 | Garibotto et al. |
| 2005/0027255 A1 | 2/2005 | Lavi et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0154353 A1 | 7/2005 | Alheidt |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197626 A1 | 9/2005 | Moberg et al. |
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0245956 A1 | 11/2005 | Steinemann et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0206057 A1 | 9/2006 | Deruntz et al. |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0079894 A1 | 4/2007 | Kraus et al. |
| 2007/0118405 A1 | 5/2007 | Campbell et al. |
| 2007/0149921 A1 | 6/2007 | Michels |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0265568 A1 | 11/2007 | Tsals et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0097387 A1 | 4/2008 | Spector |
| 2008/0108951 A1 | 5/2008 | Jerde et al. |
| 2008/0119794 A1 | 5/2008 | Alheidt |
| 2008/0140006 A1 | 6/2008 | Eskuri et al. |
| 2008/0140014 A1 | 6/2008 | Miller et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0221523 A1 | 9/2008 | Moberg et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |

(56) References Cited

U.S. PATENT DOCUMENTS

| | | |
|---|---|---|
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0105663 A1 | 4/2009 | Brand et al. |
| 2009/0124977 A1 | 5/2009 | Jensen |
| 2009/0143730 A1 | 6/2009 | De et al. |
| 2009/0143735 A1 | 6/2009 | De et al. |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259143 A1 | 10/2009 | Bakhtyari-Nejad-Esfahani |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326472 A1* | 12/2009 | Carter ............ A61M 5/14216 604/180 |
| 2009/0326509 A1 | 12/2009 | Muse et al. |
| 2010/0010455 A1 | 1/2010 | Elahi et al. |
| 2010/0018334 A1 | 1/2010 | Lessing |
| 2010/0030156 A1 | 2/2010 | Beebe et al. |
| 2010/0030198 A1 | 2/2010 | Beebe et al. |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0160894 A1 | 6/2010 | Julian et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0241103 A1 | 9/2010 | Kraft et al. |
| 2010/0256486 A1 | 10/2010 | Savage |
| 2010/0264931 A1 | 10/2010 | Lindegger et al. |
| 2010/0268169 A1 | 10/2010 | Llewellyn-Hyde et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0166509 A1 | 7/2011 | Gross |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0224646 A1 | 9/2011 | Yodfat et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Brüggemann et al. |
| 2012/0041414 A1 | 2/2012 | Estes et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0109059 A1 | 5/2012 | Ranalletta et al. |
| 2012/0109066 A1 | 5/2012 | Chase |
| 2012/0118777 A1 | 5/2012 | Kakiuchi et al. |
| 2012/0123387 A1 | 5/2012 | Gonzalez et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Brüggemann et al. |
| 2012/0184917 A1 | 7/2012 | Bom et al. |
| 2012/0226234 A1 | 9/2012 | Bazargan et al. |
| 2012/0238961 A1 | 9/2012 | Julian et al. |
| 2012/0259282 A1 | 10/2012 | Alderete et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0131589 A1 | 5/2013 | Mudd et al. |
| 2013/0131604 A1 | 5/2013 | Avery |
| 2013/0133438 A1 | 5/2013 | Kow et al. |
| 2013/0138040 A1 | 5/2013 | Weinandy |
| 2013/0153434 A1 | 6/2013 | Allanore |
| 2013/0172808 A1 | 7/2013 | Gilbert |
| 2013/0190693 A1 | 7/2013 | Ekman et al. |
| 2013/0200549 A1 | 8/2013 | Felts et al. |
| 2013/0204187 A1 | 8/2013 | Avery et al. |
| 2013/0204191 A1 | 8/2013 | Cindrich et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0245604 A1 | 9/2013 | Kouyoumjian et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0267895 A1 | 10/2013 | Hemmingsen |

(56) References Cited

U.S. PATENT DOCUMENTS

| | | |
|---|---|---|
| 2013/0296799 A1 | 11/2013 | Degtiar et al. |
| 2013/0296824 A1 | 11/2013 | Mo et al. |
| 2013/0304021 A1 | 11/2013 | Cabiri et al. |
| 2013/0310753 A1 | 11/2013 | Cabiri |
| 2013/0310807 A1 | 11/2013 | Adair et al. |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete et al. |
| 2014/0163526 A1 | 6/2014 | Cabiri et al. |
| 2014/0171881 A1* | 6/2014 | Cabiri ............... A61M 5/3287 604/263 |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0214001 A1 | 7/2014 | Mortazavi |
| 2014/0228768 A1 | 8/2014 | Eggert et al. |
| 2014/0236087 A1 | 8/2014 | Alderete et al. |
| 2014/0243786 A1 | 8/2014 | Gilbert et al. |
| 2014/0261758 A1 | 9/2014 | Wlodarczyk et al. |
| 2014/0343503 A1 | 11/2014 | Holmqvist |
| 2014/0364808 A1 | 12/2014 | Niklaus et al. |
| 2015/0005703 A1 | 1/2015 | Hutchinson et al. |
| 2015/0073344 A1 | 3/2015 | Van Damme et al. |
| 2015/0088071 A1 | 3/2015 | Cabiri |
| 2015/0112278 A1 | 4/2015 | Ray et al. |
| 2015/0119798 A1 | 4/2015 | Gross et al. |
| 2015/0157806 A1 | 6/2015 | Knutsson |
| 2015/0202375 A1 | 7/2015 | Schabbach et al. |
| 2015/0374926 A1 | 12/2015 | Gross et al. |
| 2016/0030665 A1 | 2/2016 | Cabiri |
| 2016/0051756 A1 | 2/2016 | Cabiri |
| 2016/0144117 A1 | 5/2016 | Chun |
| 2016/0151586 A1 | 6/2016 | Kemp |
| 2016/0175515 A1 | 6/2016 | Mccullough |
| 2016/0184512 A1 | 6/2016 | Marbet et al. |
| 2016/0193406 A1 | 7/2016 | Cabiri |
| 2016/0199590 A1 | 7/2016 | Schabbach et al. |
| 2016/0213840 A1 | 7/2016 | Schabbach et al. |
| 2016/0220755 A1 | 8/2016 | Lanigan et al. |
| 2016/0228652 A1 | 8/2016 | Cabiri et al. |
| 2016/0296713 A1 | 10/2016 | Schader et al. |
| 2016/0296716 A1 | 10/2016 | Cabiri et al. |
| 2016/0331900 A1 | 11/2016 | Wei |
| 2016/0339168 A1 | 11/2016 | Hutchinson et al. |
| 2016/0346478 A1 | 12/2016 | Bar-El et al. |
| 2016/0354553 A1 | 12/2016 | Anderson et al. |
| 2017/0007774 A1 | 1/2017 | Brockmeier |
| 2017/0043092 A1 | 2/2017 | Murakami et al. |
| 2017/0058349 A1 | 3/2017 | Levy et al. |
| 2017/0175859 A1 | 6/2017 | Brockmeier |
| 2017/0246399 A1 | 8/2017 | Forlani et al. |
| 2017/0246403 A1 | 8/2017 | Cowe et al. |
| 2018/0028765 A1 | 2/2018 | Waller et al. |
| 2018/0133413 A1 | 5/2018 | Grant et al. |
| 2018/0214637 A1 | 8/2018 | Kemp et al. |
| 2018/0304029 A1 | 10/2018 | Koch et al. |
| 2019/0022306 A1 | 1/2019 | Gibson et al. |
| 2019/0060578 A1 | 2/2019 | Farris et al. |
| 2019/0071217 A1 | 3/2019 | Brown et al. |
| 2019/0099549 A1 | 4/2019 | Lanigan et al. |
| 2019/0175821 A1 | 6/2019 | Kamen et al. |
| 2019/0224415 A1 | 7/2019 | Dugand et al. |
| 2019/0240417 A1 | 8/2019 | Hostettler et al. |
| 2019/0328968 A1 | 10/2019 | Giambattista |
| 2020/0009323 A1 | 1/2020 | Nair et al. |
| 2020/0164151 A1 | 5/2020 | Farris et al. |
| 2020/0215270 A1 | 7/2020 | Ogawa et al. |
| 2020/0297929 A1 | 9/2020 | Zhang |
| 2020/0360602 A1 | 11/2020 | Gray et al. |
| 2021/0138157 A1 | 5/2021 | Bar-El et al. |
| 2021/0220551 A1 | 7/2021 | Dowd et al. |

FOREIGN PATENT DOCUMENTS

| | | |
|---|---|---|
| CN | 1211454 | 3/1999 |
| CN | 1440301 | 9/2003 |
| CN | 1486198 | 3/2004 |
| CN | 1505535 A | 6/2004 |
| CN | 1747683 A | 3/2006 |
| CN | 1753699 | 3/2006 |
| CN | 1863564 | 11/2006 |
| CN | 1863566 A | 11/2006 |
| CN | 1951513 | 4/2007 |
| CN | 101090749 A | 12/2007 |
| CN | 101128228 | 2/2008 |
| CN | 101227943 A | 7/2008 |
| CN | 101448536 A | 6/2009 |
| CN | 101461976 | 6/2009 |
| CN | 101522235 A | 9/2009 |
| CN | 101522239 | 9/2009 |
| CN | 101541362 A | 9/2009 |
| CN | 101641126 A | 2/2010 |
| CN | 101687075 | 3/2010 |
| CN | 101784297 | 7/2010 |
| CN | 101868273 A | 10/2010 |
| CN | 201692438 U | 1/2011 |
| CN | 102038998 | 5/2011 |
| CN | 102089024 | 6/2011 |
| CN | 201941304 U | 8/2011 |
| CN | 102186733 A | 9/2011 |
| CN | 102245235 | 11/2011 |
| CN | 102378638 A | 3/2012 |
| CN | 102438679 | 5/2012 |
| CN | 102458512 | 5/2012 |
| CN | 102464145 | 5/2012 |
| CN | 202236675 | 5/2012 |
| CN | 102639174 | 8/2012 |
| CN | 102648016 | 8/2012 |
| CN | 102711868 | 10/2012 |
| CN | 102883761 | 1/2013 |
| CN | 103025369 | 4/2013 |
| CN | 103118737 | 5/2013 |
| CN | 103228303 | 7/2013 |
| CN | 203044048 | 7/2013 |
| CN | 103619378 | 3/2014 |
| CN | 103648561 | 3/2014 |
| CN | 103702699 | 4/2014 |
| CN | 103732277 | 4/2014 |
| CN | 103764197 | 4/2014 |
| CN | 103921966 | 7/2014 |
| CN | 103974734 | 8/2014 |
| CN | 103998082 | 8/2014 |
| CN | 203874209 | 10/2014 |
| CN | 104411350 | 3/2015 |
| CN | 104487116 | 4/2015 |
| CN | 104519933 | 4/2015 |
| CN | 104619366 | 5/2015 |
| CN | 105102025 A | 11/2015 |
| CN | 105749383 | 7/2016 |
| DE | 0855313 C | 11/1952 |
| DE | 855313 C | 11/1952 |
| DE | 1064693 B | 9/1959 |
| DE | 19518807 A1 | 12/1995 |
| DE | 19717107 A1 | 11/1998 |

(56) References Cited

FOREIGN PATENT DOCUMENTS

| | | |
|---|---|---|
| EP | 0017412 A1 | 10/1980 |
| EP | 0222656 A1 | 5/1987 |
| EP | 0401179 A1 | 12/1990 |
| EP | 0851774 A1 | 7/1998 |
| EP | 0925082 A1 | 6/1999 |
| EP | 1003581 A1 | 5/2000 |
| EP | 1124600 A1 | 8/2001 |
| EP | 1219312 A2 | 7/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 1654018 | 11/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2393535 B1 | 3/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2819724 B1 | 3/2019 |
| FR | 2770136 A1 | 4/1999 |
| GB | 2301035 | 11/1996 |
| GB | 2436526 A | 10/2007 |
| JP | 62-112566 A | 5/1987 |
| JP | S62112566 A | 5/1987 |
| JP | 01-172843 U | 12/1989 |
| JP | H01172843 U | 12/1989 |
| JP | 05-062828 A | 3/1993 |
| JP | H05062828 A | 3/1993 |
| JP | 07-194701 A | 8/1995 |
| JP | H07194701 A | 8/1995 |
| JP | 3035448 U | 3/1997 |
| JP | 09-505758 A | 6/1997 |
| JP | 11-507260 A | 6/1999 |
| JP | H11507260 A | 6/1999 |
| JP | 2000-107289 A | 4/2000 |
| JP | 2000-515394 A | 11/2000 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-534061 A | 11/2003 |
| JP | 2004-501721 A | 1/2004 |
| JP | 2004-512100 A | 4/2004 |
| JP | 2003-527138 A | 8/2005 |
| JP | 2005-523127 A | 8/2005 |
| JP | 2005-527249 A | 9/2005 |
| JP | 2005-270629 A | 10/2005 |
| JP | 2006-507067 A | 3/2006 |
| JP | 2006-510450 A | 3/2006 |
| JP | 2006-525046 A | 11/2006 |
| JP | 2007-509661 A | 4/2007 |
| JP | 2007-306990 A | 11/2007 |
| JP | 2008-534131 A | 8/2008 |
| JP | 2008-220961 A | 9/2008 |
| JP | 2008272084 | 11/2008 |
| JP | 2009-502273 A | 1/2009 |
| JP | 2009-101093 A | 5/2009 |
| JP | 2010-540054 A | 12/2010 |
| JP | 2010-540156 A | 12/2010 |
| JP | 2011-136153 A | 7/2011 |
| JP | 2012-100927 A | 5/2012 |
| JP | 4947871 B2 | 6/2012 |
| JP | 2013-500811 A | 1/2013 |
| JP | 2013-505433 A | 2/2013 |
| JP | 2013-517095 A | 5/2013 |
| JP | 2013-519473 A | 5/2013 |
| JP | 2013-530778 A | 8/2013 |
| JP | 2013-531520 A | 8/2013 |
| JP | 2013-531540 A | 8/2013 |
| JP | 2014-030489 A | 2/2014 |
| JP | 2014-515669 A | 7/2014 |
| JP | 2014-518743 A | 8/2014 |
| JP | 2015-514486 A | 5/2015 |
| JP | 2016-525428 A | 8/2016 |
| JP | 2016-530016 A | 9/2016 |
| MX | PA06003233 | 6/2006 |
| WO | 90/09202 A1 | 8/1990 |
| WO | 93/07922 A1 | 4/1993 |
| WO | 94/07553 A1 | 4/1994 |
| WO | 94/15660 A1 | 7/1994 |
| WO | 95/13838 A1 | 5/1995 |
| WO | 96/09083 A1 | 3/1996 |
| WO | 96/32975 A1 | 10/1996 |
| WO | 97/00091 A1 | 1/1997 |
| WO | 97/10012 A1 | 3/1997 |
| WO | 97/21457 A1 | 6/1997 |
| WO | 97/33638 A1 | 9/1997 |
| WO | 98/57683 A1 | 12/1998 |
| WO | 98/57686 A1 | 12/1998 |
| WO | 99/29151 A1 | 6/1999 |
| WO | 99/38554 A1 | 8/1999 |
| WO | 99/59665 A1 | 11/1999 |
| WO | 00/25844 A1 | 5/2000 |
| WO | 00/69509 A1 | 11/2000 |
| WO | 01/30415 A2 | 5/2001 |
| WO | 01/30421 A2 | 5/2001 |
| WO | 01/70304 A1 | 9/2001 |
| WO | 01/72357 A2 | 10/2001 |
| WO | 01/87384 A1 | 11/2001 |
| WO | 01/89607 A2 | 11/2001 |
| WO | 01/89613 A1 | 11/2001 |
| WO | 02/02165 A2 | 1/2002 |
| WO | 02/04049 A1 | 1/2002 |
| WO | 02/34315 A1 | 5/2002 |
| WO | 02/38204 A2 | 5/2002 |
| WO | 02/56934 A2 | 7/2002 |
| WO | 02/56943 A2 | 7/2002 |
| WO | 02/72182 A1 | 9/2002 |
| WO | 03/62672 A1 | 7/2003 |
| WO | 03/90833 A1 | 11/2003 |
| WO | 2004/000397 A1 | 12/2003 |
| WO | 2004/032990 A2 | 4/2004 |
| WO | 2004/098684 A2 | 11/2004 |
| WO | 2004/105841 A1 | 12/2004 |
| WO | 2005/018703 A2 | 3/2005 |
| WO | 2005/037350 A2 | 4/2005 |
| WO | 2005/070485 A1 | 8/2005 |
| WO | 2005/072795 A2 | 8/2005 |
| WO | 2006/018617 A1 | 2/2006 |
| WO | 2006/037434 A1 | 4/2006 |
| WO | 2006/052737 A1 | 5/2006 |
| WO | 2006/069380 A1 | 6/2006 |
| WO | 2006/102676 A1 | 9/2006 |
| WO | 2006/104806 A2 | 10/2006 |
| WO | 2006/121921 A2 | 11/2006 |
| WO | 2007/017052 A1 | 2/2007 |
| WO | 2007/051563 A1 | 5/2007 |
| WO | 2007/056504 A1 | 5/2007 |
| WO | 2007/066152 A2 | 6/2007 |
| WO | 2007/073228 A1 | 6/2007 |
| WO | 2007/119178 A2 | 10/2007 |
| WO | 2008/001377 A2 | 1/2008 |
| WO | 2008/014908 A1 | 2/2008 |
| WO | 2008/057976 A2 | 5/2008 |
| WO | 2008/072229 A2 | 6/2008 |
| WO | 2008/076459 A1 | 6/2008 |
| WO | 2008/078318 A2 | 7/2008 |
| WO | 2009/019438 A1 | 2/2009 |
| WO | 2009/022132 A2 | 2/2009 |
| WO | 2009/043000 A1 | 4/2009 |

(56) References Cited

FOREIGN PATENT DOCUMENTS

| | | |
|---|---|---|
| WO | 2009/043564 A1 | 4/2009 |
| WO | 2009/044401 A2 | 4/2009 |
| WO | 2009/046989 A2 | 4/2009 |
| WO | 2009/069064 A1 | 6/2009 |
| WO | 2009/125398 A2 | 10/2009 |
| WO | 2009/144085 A2 | 12/2009 |
| WO | 2010/078227 A1 | 7/2010 |
| WO | 2010/078242 A1 | 7/2010 |
| WO | 2010/089313 A1 | 8/2010 |
| WO | 2011/075105 A1 | 6/2011 |
| WO | 2011/090955 A1 | 7/2011 |
| WO | 2011/090956 A2 | 7/2011 |
| WO | 2011/101378 A1 | 8/2011 |
| WO | 2011/110872 A1 | 9/2011 |
| WO | 2011/124631 A1 | 10/2011 |
| WO | 2011/129175 A1 | 10/2011 |
| WO | 2011/131778 A1 | 10/2011 |
| WO | 2011/131780 A2 | 10/2011 |
| WO | 2011/131781 A1 | 10/2011 |
| WO | 2011/133823 A1 | 10/2011 |
| WO | 2011/156373 A1 | 12/2011 |
| WO | 2012/003221 A1 | 1/2012 |
| WO | 2012/032411 A2 | 3/2012 |
| WO | 2012/040528 A1 | 3/2012 |
| WO | 2012/145752 A2 | 10/2012 |
| WO | 2012/160157 A1 | 11/2012 |
| WO | 2012/168691 A1 | 12/2012 |
| WO | 2013013081 | 1/2013 |
| WO | 2013013081 A1 | 1/2013 |
| WO | 2013/036602 A1 | 3/2013 |
| WO | 2013/058697 A1 | 4/2013 |
| WO | 2013/115843 A1 | 8/2013 |
| WO | 2014/132293 A1 | 9/2014 |
| WO | 2014166904 | 10/2014 |
| WO | 2014166904 A1 | 10/2014 |
| WO | 2014173771 | 10/2014 |
| WO | 2014173771 A1 | 10/2014 |
| WO | 2014/179117 A1 | 11/2014 |
| WO | 2014/179774 A1 | 11/2014 |
| WO | 2014/194183 A2 | 12/2014 |
| WO | 2014191038 | 12/2014 |
| WO | 2014191038 A1 | 12/2014 |
| WO | 2015015379 | 2/2015 |
| WO | 2015015379 A1 | 2/2015 |
| WO | 2015032740 | 3/2015 |
| WO | 2015032740 A1 | 3/2015 |
| WO | 2015/048791 A1 | 4/2015 |
| WO | 2015/048803 A2 | 4/2015 |
| WO | 2015059192 | 4/2015 |
| WO | 2015059192 A1 | 4/2015 |
| WO | 2015/078868 A1 | 6/2015 |
| WO | 2015/091758 A1 | 6/2015 |
| WO | 2015/091850 A1 | 6/2015 |
| WO | 2015/114158 A1 | 8/2015 |
| WO | 2015/114428 A1 | 8/2015 |
| WO | 2015/118358 A1 | 8/2015 |
| WO | 2015/163009 A1 | 10/2015 |
| WO | 2016/087626 A1 | 6/2016 |
| WO | 2016/087627 A1 | 6/2016 |
| WO | 2016/141082 A1 | 9/2016 |
| WO | 2017/022639 A1 | 2/2017 |
| WO | 2017/161076 A1 | 9/2017 |
| WO | 2018/222521 A1 | 12/2018 |
| WO | 2019/224782 A1 | 11/2019 |
| WO | 2020/120087 A1 | 6/2020 |
| WO | 2020/193468 A1 | 10/2020 |

OTHER PUBLICATIONS

Communication Pursuant to Rules 161 and 162 dated Apr. 6, 2018 in EP Application No. 16784688.0.
Copaxone(Registered), Innovative Drugs, Teva Pharmaceuticals, downloaded from webpage: http://levapharm.com/copaxone/, Download date: Jan. 2009, original posting date: unknown, 3 pages.
Daikyo Crystal Zenith(Registered) polymer, Manufactured by Daikyo Seiko, Lid. (Jun. 25, 2008).
Definition of Monolithic. In Merriam-Webster's online dictionary. Retrieved from https://www.merriam-webster.com/dictionary/monolithic (Year: 2021).
English translation of an Office Action dated Jan. 30, 2013 in CN Application No. 200880117084.X.
English translation of an Office Action dated Mar. 5, 2014 in CN Application No. 200880117084.X.
European Search Report (Partial) dated Mar. 8, 2017 in EP Application 16193157.1.
Extended European Search Report dated Aug. 7, 2014 in EP Application No. 1417477.4.
Extended European Search Report dated Feb. 12, 2018 in EP Application No. 17191756.0.
Extended European Search Report dated Feb. 13, 2017 in EP Application No. 16171626.1.
Extended European Search Report dated Feb. 23, 2015 in EP Application No. 14166591.9.
Extended European Search Report dated Feb. 23, 2015 in EP Application No. 14166596.8.
Extended European Search Report dated Jul. 3, 2017 in EP Application No. 16190054.3.
Extended European Search Report dated Mar. 27, 2014 in EP Application No. 14154717.4.
Extended European Search Report dated Mar. 8, 2016 in EP Application No. 14166592.7.
Extended European Search Report dated Nov. 10, 2016 in EP Application No. 08808111.2.
Extended European Search Report dated Jul. 28, 2020 in European Application No. 20172466.3.
Extended Search Report dated Aug. 7, 2014 in EP Application No. 14171477.4.
Extended Search Report dated Jul. 7, 2017 in EP Application No. 16193157.1.
Int'l Preliminary Report on Patentability dated Nov. 22, 2017 in Int'l Application No. PCT/US2016/068371.
Int'l Search Report and Written Opinion dated Jan. 12, 2011 in Int'l Application No. PCT/US2010/048556; Written Opinion.
Int'l Search Report and Written Opinion dated Jan. 26, 2017 in Int'l Application No. PCT/US2016/056213.
Int'l Search Report and Written Opinion dated Mar. 27, 2017 in Int'l Application No. PCT/US2016/056247.
Int'l Search Report and Written Opinion dated Apr. 21, 2017 in Int'l Application No. PCT/US2016/068367.
Int'l Search Report and Written Opinion dated May 15, 2017 in Int'l Application No. PCT/US2016/068371.
Int'l Search Report and Written Opinion dated Jul. 6, 2017 in Int'l Application No. PCT/US2017/022966.
Int'l Search Report and Written Opinion dated Nov. 28, 2016 in Int'l Application No. PCT/US2016/056218.
Int'l Search Report and Written Opinion dated Dec. 2, 2016 in Int'l Application No. PCT/US2016/056210.
Int'l Search Report and Written Opinion dated Dec. 5, 2016 in Int'l Application No. PCT/US2016/056233.
Int'l Search Report and Written Opinion dated Dec. 8, 2016 in Inl'l Application No. PCT/US2016/056227.
Int'l Search Report and Written Opinion dated Dec. 15, 2016 in Inl'l Application No. PCT/US2016/056258.
Int'l Search Repport (Partial), dated Dec. 20, 2016 in Int'l Application No. PCT/US2016/056247.
Int'l Preliminary Report on Patentability dated Jan. 8, 2018 in Int'l Application No. PCT/US2016/056218.
Int'l Preliminary Report on Patentability dated Apr. 7, 2010 in Int'l Application No. PCT/IL2008/001312.
Int'l Preliminary Report on Patentability dated Aug. 2, 2012 in Int'l Application No. PCT/US2011/021604.
Int'l Preliminary Report on Patentability dated Feb. 7, 2013 in Int'l Application No. PCT/US11/21605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.

(56) References Cited

OTHER PUBLICATIONS

Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Search Report and Written Opinion dated Apr. 3, 2014 in Int'l Application No. PCT/US2013/078040.
Int'l Search Report and Written Opinion dated Aug. 5, 2013 in Int'l Application No. PCT/US2013/033118.
Office Action dated Nov. 6, 2015 in U.S. Appl. No. 14/715,791 by Cabiri.
Office Action dated Oct. 6, 2020 in Japanese Application No. 2018-538527.
Partial European Search Report dated Nov. 24, 2015 in EP Application No. 14166592.7.
Search Report dated Oct. 14, 2016 in CN Application No. 2014101783742.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
U.S. Appl. No. 13/733,516 by Cabiri, filed Jan. 3, 2013.
U.S. Appl. No. 13/873,335 by Filman, filed Apr. 30, 2013.
U.S. Appl. No. 13/874,017 by Cabiri, filed Apr. 30, 2013.
U.S. Appl. No. 13/874,085 by Cabiri, filed Apr. 30, 2013.
U.S. Appl. No. 13/874,121 by Degtiar, filed Apr. 30, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/553,399 by Cabiri, filed Nov. 25, 2014.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
U.S. Appl. No. 29/479,307 by Norton, filed Jan. 14, 2014.
U.S. Appl. No. 60/997,459, filed Oct. 2, 2007.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillab- le-syringe-system, Download date: Jan. 2009, original posting date: Jun. 2008, 2 pages.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 30, 2018 in U.S. Appl. No. 14/850,450 by Gross.
Office Action dated Mar. 31, 2015 in JP Application No. 2012-550068.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Office Action dated May 18, 2018 in EP 14166591.9.
Office Action dated May 23, 2014 in U.S. Appl. No. 13/472,112 by Cabiri.
Office Action dated May 24, 2017 in U.S. Appl. No. 13/874,121, by Degtiar.
Office Action dated May 25, 2016 in U.S. Appl. No. 14/874,017 by Cabiri.
Office Action dated May 25, 2021 in Japanese Office Action 2018-538073.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 2014101836665.
Office Action dated May 5, 2015 in CN Application No. 201180006571.0.
Office Action dated May 7, 2015 in JP Application No. 2012-550069.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 2, 2014 in CN Application No. 201180006571.0.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2016 in U.S. Appl. No. 13/874,017, by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 8, 2017 in U.S. Appl. No. 13/874,121, by Degtiar.
Office Action dated Oct. 13, 2020 in Japanese Application No. 2018-538073.
Office Action dated Oct. 2, 2018 in JP Application No. 2018-535062 (Year: 2018).
Office Action dated Oct. 28, 2011 in U.S. Appl. No. 12/615,828.
Office Action dated Oct. 28, 2016 in CN Application No. 2014101783742.
Office Action dated Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2014 in U.S. Appl. No. 13/873,335.
Office Action dated Sep. 18, 2015 in U.S. Appl. No. 13/874,085 by Cabiri.
Office Action dated Sep. 2, 2010 in U.S. Appl. No. 12/244,688 by Gross.
Office Action dated Sep. 2, 2014 in JP Application No. 2012-550068.
Office Action dated Sep. 2, 2014 in JP Application No. 2012-550069.

(56) References Cited

OTHER PUBLICATIONS

Office Action dated Sep. 28, 2017 in IN Application No. 2528/DELNP/2010.
Office Action dated Sep. 29, 2013 in CN Application No. 201080040968.7.
Office Action dated Sep. 30, 2010 in U.S. Appl. No. 12/689,250, by Cabiri.
Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action dated Aug. 17, 2021 in Indian Application No. 201827027625.
Office Action dated Feb. 20, 2015 in U.S. Appl. No. 13/521,181 by Cabiri.
Int'l Search Report and Written Opinion dated Jan. 7, 2014 in Int'l Application No. PCT/US2013/065211.
Int'l Search Report and Written Opinion dated Jul. 12, 2017 in Int'l Application No. PCT/US2016/056238.
Int'l Search Report and Written Opinion dated Jul. 26, 2013 in Int'l Application No. PCT/US2012/039465.
Int'l Search Report and Written Opinion dated Jul. 31, 2014 in Int'l Application No. PCT/US2014/033598.
Int'l Search Report and Written Opinion dated May 13, 2009 in Int'l Application No. PCT/IL2008/001312.
Int'l Search Report dated Apr. 26, 2010 in Int'l Application No. PCT/US2009/069552.
Int'l Search Report dated Jun. 17, 2011 in Int'l Application No. PCT/US2011/021604.
Int'l Search Report dated Oct. 12, 2011 in Int'l Application No. PCT/US11/21605.
Int'l Search Report dated Sep. 22, 2011 in Int'l Application No. PCT/IL11/00368; Written Opinion.
Int'l Written Opinion dated Jul. 19, 2012 in Int'l Application No. PCT/US11/21605.
Inte'l Search Report and Written Opinion dated Nov. 30, 2016 in Int'l Application No. PCT/US2016/056223.
International Preliminary Report on Patentability and Written Opinion dated Jul. 5, 2011 in International Application No. PCT/US2009/069552.
Notice of Allowance dated Aug. 24, 2015 in U.S. Appl. No. 29/479,307 by Norton.
Ofice Action dated Sep. 21, 2010 in U.S. Appl. No. 12/244,666 by Gross.
Office Action dated Apr. 22, 2016 in CN Application No. 2014102892041.
Office Action dated Apr. 5, 2010 in U.S. Appl. No. 12/244,666 by Gross.
Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 14, 2017 in CN Application No. 201410178318.9.
Office Action dated Aug. 15, 2013 in CN Application No. 200880117084.X.
Office Action dated Aug. 26, 2014 in CN Application No. 201180006567.4.
Office Action dated Aug. 6, 2014 in EP Appl. No. 11 707 942.6.
Office Action dated Dec. 1, 2015 in CN Application No. 201410289204.1.
Office Action dated Dec. 10, 2013 in CN Application No. 201180006567.4.
Office Action dated Dec. 15, 2017 in U.S. Appl. No. 15/269,248, by Cabiri.
Office Action dated Dec. 17, 2013 in JP Application No. 2012-529808.
Office Action dated Dec. 4, 2017 in CN Application No. 201410178374.2.
Office Action dated Dec. 9, 2016 in U.S. Appl. No. 14/593,051, by Gross.
Office Action dated Feb. 16, 2017 in CN Application No. 2014101783189.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6.
Office Action dated Jan. 10, 2017 in U.S. Appl. No. 14/193,692, by Gross.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 28, 2020 in Japanese Application No. 2018-538074.
Office Action dated Jul. 3, 2017 in CN Application No. 2014101783742.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595.
Office Action dated Jun. 4, 2015 in U.S. Appl. No. 13/667,739 by Cabiri.
Office Action dated Jun. 9, 2017 in EP Application No. 14166591.9.

\* cited by examiner

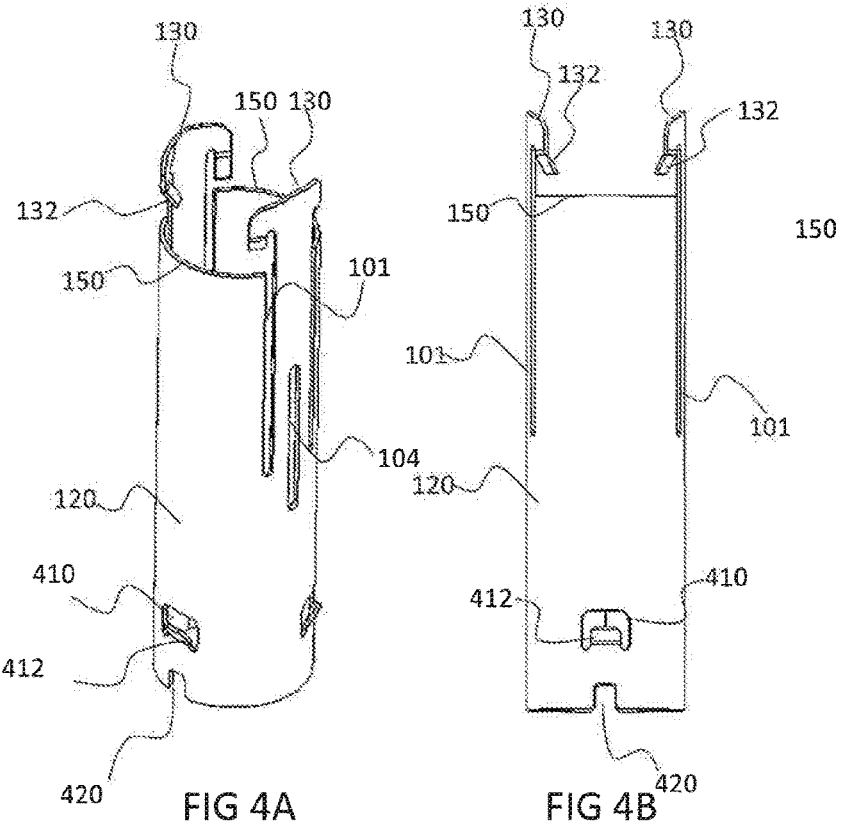
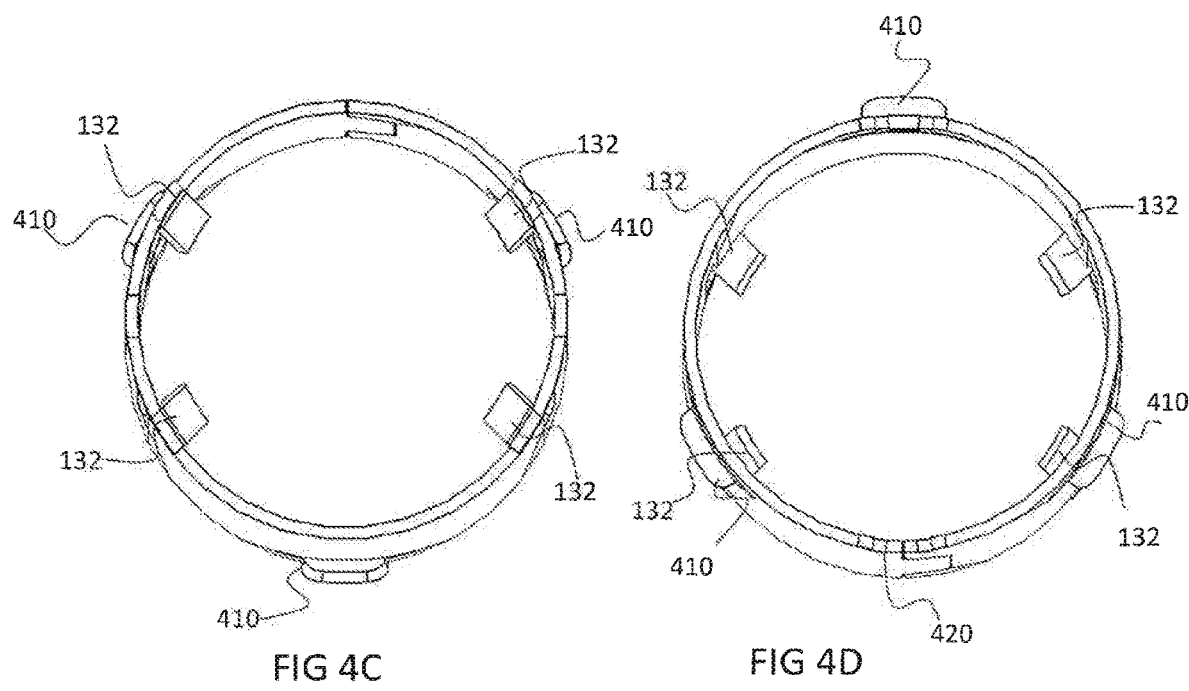
FIG 4A  FIG 4B  FIG 4C  FIG 4D

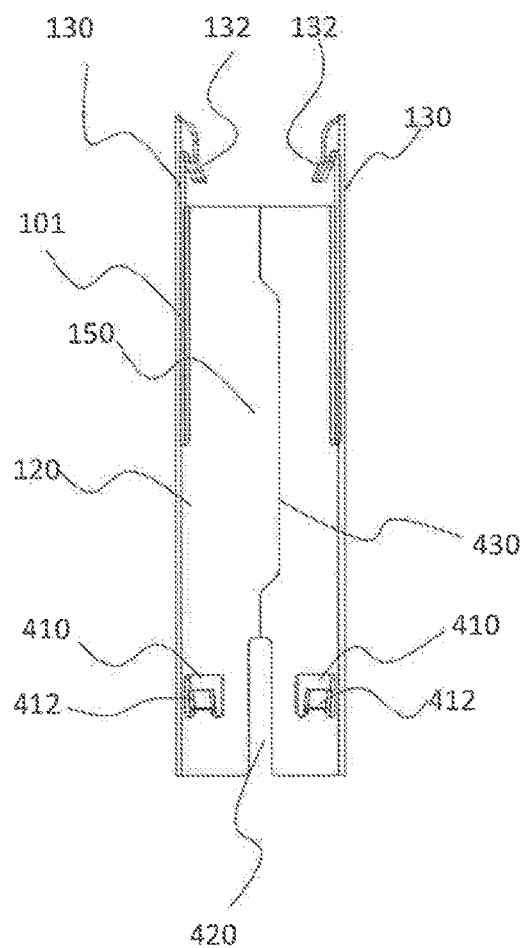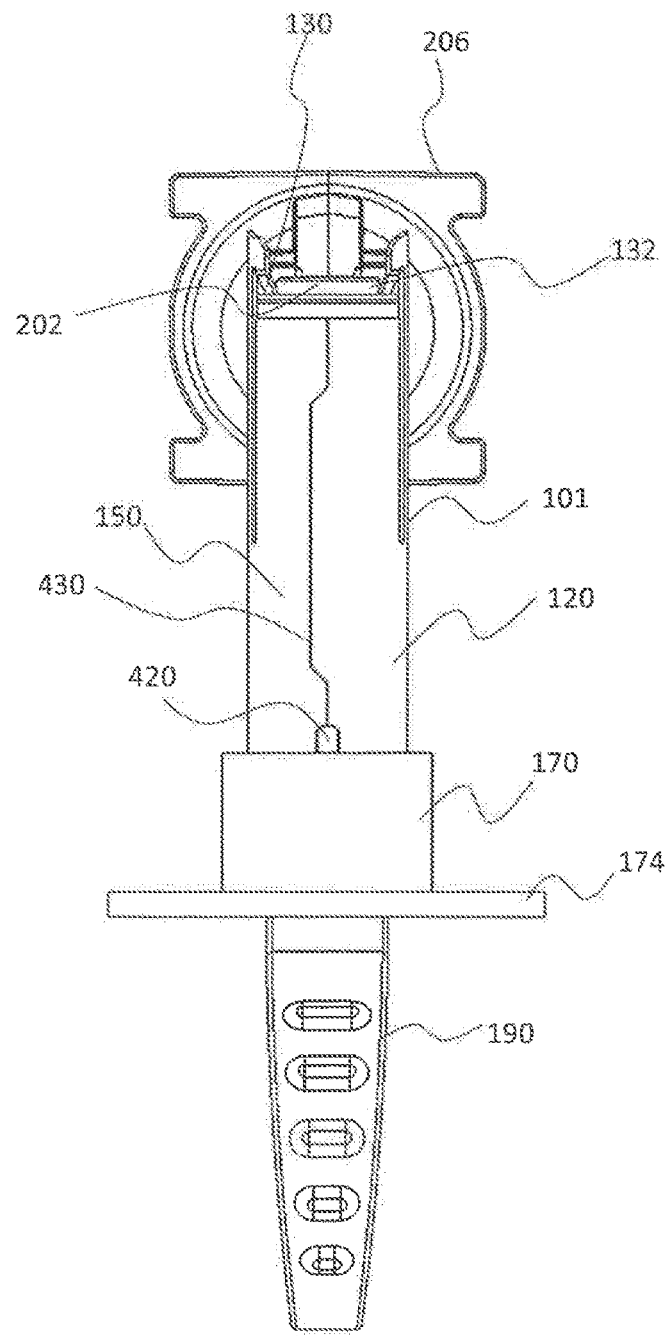
FIG 4E
FIG 4F

INJECTOR NEEDLE CAP AND/OR LINER REMOVER

CROSS-REFERENCE TO RELATED APPLICATION

This application is a divisional application of U.S. patent application Ser. No. 15/766,670, filed Apr. 6, 2018, which is a U.S. National Phase Patent Application of International Application No. PCT/US16/56247, filed Oct. 10, 2016, which is a continuation of U.S. patent application Ser. No. 15/204,542, filed Jul. 7, 2016, which claims the benefit of U.S. Provisional Patent Application No. 62/281,536, filed Jan. 21, 2016, and U.S. Provisional Patent Application No. 62/284,806, filed Oct. 9, 2015; and is a continuation of U.S. patent application Ser. No. 15/269,248, filed Sep. 19, 2016, the disclosures of which are incorporated herein by reference.

FIELD AND BACKGROUND OF THE INVENTION

The present invention, in some embodiments thereof, relates to a needle cap remover and, more particularly, but not exclusively, to a bifurcated needle cap remover.

U.S. Patent Application No. US 2012/0238961 discloses "a needle shield remover that reliably engages with a distal cap of an automatic injection device and with one or more needle shields coupled to a syringe of the device. When a user removes the distal cap, the needle shield remover reliably removes the needle shields (e.g., a soft needle shield and a rigid needle shield) from the syringe, thereby exposing the injection needle for performing an injection. In an exemplary assembly method, a needle shield remover is engaged to a needle shield coupled to a syringe, prior to insertion of the syringe and needle shield remover assembly into a housing of the device. This exemplary assembly method allows visual inspection, outside the housing of the device, to ensure that the needle shield remover is correctly and reliably engaged to the needle shield before the syringe and needle shield remover assembly is inserted into the housing".

U.S. Pat. No. 6,843,782 discloses "a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject".

International Patent Application Publication No. WO 2015/048791 discloses "a method of preparing a compound device for use. The device may include a sealed component and an active outer surface. The outer surface may be protected by a surface cover. Preparing the device may include activating the active outer surface by removing the surface cover and exposing an internal portion of the sealed component to the exterior of the device by unsealing the sealed component and synchronizing the activating and said unsealing using a coupler attached to the surface cover and the sealed component."

SUMMARY OF THE INVENTION

Example 1. A device for removing a needle cap, the needle cap shielding a needle of an injector system, the device comprising: an elongated hollow body, having a distal end sized and shaped to at least partially envelop the needle cap; and at least one snap coupled to at least one respective element of the elongated body; the elongated body having a closed and open configuration, wherein the closed configuration is defined by the at least one snap defining a width smaller than a width of a top sill of the needle cap, and the open configuration is defined by the at least one snap having a width wide enough to fit at least the width of the top sill; wherein the hollow body in the closed configuration is shaped to hold the at least one snap overhanging a top sill of the needle cap with the hollow body enveloping a lower portion of the needle cap.

Example 2. The device of example 1, wherein the at least one snap inflects towards a central axis of the needle cap, being angled with respect to the axis.

Example 3. The device of any of examples 1-2, comprising at least two snaps coupled to at least two respective elements being at least two elastic arms having an open configuration defined by elastically deflecting away from the central axis of the needle cap, and wherein once the at least two snaps are pushed beyond the top sill of the needle cap, the elastic arms return to their closed configuration and the at least two snaps overhang the top sill of the needle cap.

Example 4. The device of example 3, wherein each of the at least two elastic arms is defined as a surface between two slits, the two slits extend from the distal end of the elongated hollow body.

Example 5. The device of example 4, wherein the slits extend to a length having a range of between about 20% and about 60% of a length of the elongated hollow body.

Example 6. The device of any of examples 4-5, wherein each of the two slits have a width having a range of about 0.5 mm and about 1.5 mm.

Example 7. The device of any of examples 4-6, further comprising at least one intermediate longitudinal slit provided in the surface between the two slits.

Example 8. The device of any of examples 3-7, wherein the at least two arms encompass no more than about 40% of a circumference of the elongated hollow body.

Example 9. The device of example 8, wherein the at least two arms are symmetrically positioned around the circumference of the elongated hollow body.

Example 10. The device of any of examples 1-9, wherein the elongated body is configured to be pushed over a needle cap using a force having a range of about 50 g and about 200 g.

Example 11. The device of any of examples 1-10, wherein the elongated body further comprises at least two guides along its inner surface and oriented along a longitudinal axis of the elongated body, the at least two guides sized and shaped to accommodate complementary elements positioned on an outer surface of the needle cap.

Example 12. The device of any of examples 1-11, further comprising a connector sized and shaped to fit a proximal portion of the body, the connector comprising a user handle having a protruding element.

Example 13. The device of example 12, wherein the elongated body further comprises at least one interlocking element complementary to an interlocking member positioned in the connector, inhibiting a lateral movement of the elongated body with respect to the connector.

Example 14. A system for medicament delivery, comprising: a cartridge containing a medicament and being in fluid communication with a needle, the needle enveloped by a needle cap; a housing for containing the cartridge and having an orifice for allowing access to the needle cap and its associated needle; and a needle cap remover device comprising: at least two elastic arms coupled to define an unstressed width greater than the outside of a width of the top sill of the needle cap, the elastic arms envelop at least a portion of the needle cap, wherein a proximal end of the elastic arms can be accessed through the orifice; and at least two snaps, each coupled to a distal end of each of the at least two elastic arms, the snaps defining an unstressed width smaller than the width of the top sill of the needle cap; wherein the at least two snaps overhang the top sill of the needle cap, and when the proximal end of the elastic arms is pulled, the snaps cause the needle cap to pull with the needle cap remover device.

Example 15. The system of example 14, wherein each of the at least two snaps comprise two hooks inflecting towards a central axis of the needle cap and being angled towards the top surface of the needle cap.

Example 16. The system of example 15, wherein the hooks are symmetrically arranged around a central axis of the top sill of the needle cap.

Example 17. The system of any of examples 15-16, wherein the needle cap remover device comprises two of the at least two arms, and wherein each of the two arms comprises two of the hooks.

Example 18. The system of any of examples 14-17, further comprising an adhesive layer having a protective liner, the adhesive layer connected to the housing, wherein the protective liner extends beyond a surface of the housing and positioned between the cap remover body and a connector.

Example 19. The system of example 18, wherein when the needle cap remover is pulled linearly the protective liner is peeled from the housing.

Example 20. The system of any of examples 14-19, wherein pulling the cap remover body together with the enveloped needle cap requires a force being no more than 1 kg at most.

Example 21. A method of assembling a needle cap remover onto a needle cap, comprising: aligning a longitudinal axis of the needle cap remover body to be colinear with a longitudinal axis of the needle cap; inserting the distal end of the cap remover body in the direction of the top portion of the needle cap while deflecting at least two elastic elements of the cap remover body in a direction away from the central axis of the needle cap, the deflecting is provided by a plurality of hooks coupled to a distal end of the elastic members and defining a smaller perimeter than a perimeter of the needle cap; wherein the inserting is provided until the plurality of hooks extend beyond the top portion of the needle cap and snap inwardly towards the central axis of the needle cap, thereby overhanging the top portion of the needle cap, causing the elastic elements to snap from the deflecting towards the central axis of the needle cap.

Example 22. The method according to example 21, wherein the needle cap is comprised within an injector system and the method further comprises inserting the needle cap remover through an orifice in the injector system having access to the needle cap.

Example 23. The method according to any of examples 21-22, further comprising interlocking a proximal portion of the needle cap remover body with a connector having a user handle.

Example 24. The method of example 16, further comprising associating the cap remover body with a battery insulator.

Example 25. A cover for an injector having a needle, a needle cap, and a needle cap remover having a coupler for a needle cap and a user handle, the user handle having a protruding element opposite the coupler, the protruding element having a short dimension and a long dimension, the cover comprising: at least one adhesive layer covering a surface of an outside of the injector; at least one liner layer, covering the adhesive layer, an extension extending beyond the surface; a first aperture through the adhesive layer and the liner layer aligned to an opening in the surface, the first aperture sized and shaped for passage of the coupler therethrough; and a second elongated aperture, through the extension, having a length being longer than the short dimension and shorter than the long dimension of the protruding element.

Example 26. The cover according to example 25, wherein the extension and the liner are made of a single integral piece of material Example 27. The cover according to example 25, wherein the second elongated aperture has a width being smaller than a shoulder portion extending from the protruding element along its long dimension.

Example 28. The cover according to example 27, wherein the extension comprises a resilient material enabling enough stretch to pass over the shoulder and to overhang a top sill of the shoulder.

Example 29. The cover according to example 28, wherein the resilient material residing in at least a portion of a circumference of the second elongated aperture.

Example 30. The cover according to any of examples 25-29, further comprising a rigid layer surrounding at least a portion of a circumference of the second elongated aperture.

Example 31. The cover according to any of examples 25-30, wherein the first aperture having a circumference shape matching a circumference shape of the needle cap remover.

Example 32. The cover according to example 31, wherein a width of the circumference shape of the first aperture is wider than the circumference shape of the needle cap remover by no more than about 1 mm.

Example 33. The cover according to any of examples 25-32, further comprising at least one intermittent supporting layer attached to the at least one liner layer, the intermittent supporting layer is not continuous over an area of the cover;

Example 34. A method of assembling an automatic injector device having an interior volume and a base located between the interior volume and an exterior surface defined by the base, the base having an opening, the method comprising: supplying a cover having a first aperture aligned with the opening in the base, the cover having an extension extending beyond the exterior surface of the base and having a second aperture; passing a distal portion of a needle cap remover through the first aperture and the opening; coupling the distal portion to a needle cap positioned in the interior volume; bending the extension over a protruding element provided in a proximal end of the needle cap remover; the protruding element having a long dimension and a short dimension; orienting the second aperture of the cover to face the short dimension of the handle and rotating the cover onto the protruding element until the second aperture is oriented to face the long dimension.

Example 35. The method of example 34, further comprising: interlocking a cartridge having a capped needle in the inner portion of the base, the cartridge central axis perpendicular to the cover and the capped needle centrally aligned with the first aperture of the cover and the opening of the base.

Example 36. The method of any of examples 34-35, wherein the cover converts a linear movement away from the exterior surface into a peeling force on the cover.

Example 37. The method of example any of examples 34-36, further comprising sliding the second aperture along the long dimension in an offset direction from a central axis of the long dimension.

Example 38. The method of any of examples 34-37, further comprising stabilizing the extension of the cover onto the protruding element by constraining the second aperture against a widening portion of the protruding element.

Example 39. The method of example 38, wherein the constraining further includes passing the second aperture over the widening portion into a narrower portion and overhanging an edge of the second aperture over the widening portion.

Example 40. The method of any of examples 34-39, further comprising rotating the user handle such that the long dimension is not aligned with the length of the second aperture.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-E schematically illustrate an exemplary device for removing a needle cap having a bifurcated body, in accordance with some embodiments of the current invention, wherein FIG. 1A illustrates a perspective view, FIG. 1B illustrates a front view, FIG. 1C illustrates a side view, FIG. 1D illustrates a top view and FIG. 1E illustrates a perspective top view;

FIGS. 2A-C schematically illustrate an exemplary use of the cap remover in an injector device, in accordance with some embodiments of the current invention, wherein FIG. 2A illustrates an example of the device being used in an automatic injector assembly, FIG. 2B illustrates the inner cartridge and needle assembly provided in the injector of FIG. 2A, and FIG. 2C illustrates another example of the device used in an automatic injector;

FIGS. 3A-G schematically illustrate an exemplary incorporation of an adhesive liner of an injector device into the cap remover, in accordance with some embodiments of the current invention, wherein FIG. 3A illustrates a perspective side view, FIG. 3B illustrates a side view, FIG. 3C illustrates a cross sectional side view of a cap remover assembled onto a cartridge, FIG. 3D illustrates a perspective view of the injector having a device cover, FIG. 3E illustrates a front view of the injector having a device cover, FIG. 3F illustrates a perspective view of the device cover and FIG. 3G illustrates an explosive view of the device cover layers, in accordance with some embodiments of the invention;

FIGS. 4A-I schematically illustrate an exemplary needle cap remover bifurcated cover and its assembly with a needle cap, in accordance with some embodiments of the current invention, wherein FIG. 4A illustrates a perspective view, FIG. 4B illustrates a front view, FIG. 4C illustrates a side view, FIG. 4D illustrates a top view, FIG. 4E illustrates a bottom view of a needle cap remover embodiment, and FIG. 4E illustrates a second needle cap remover cover embodiment, shown as part of a cap remover device assembled on a cartridge in FIG. 4F, and FIG. 4G illustrates a cross section of a front view of a needle cap remover device being pushed onto a needle cap and FIG. 4H illustrates a cross section of the device and the needle cap after their assembly, and FIG. 4I illustrates a partial perspective close up view of the top portion of the needle cap assembled with the cap remover;

FIGS. 5A-E schematically illustrate an exemplary cap remover connector having a handle, in accordance with some embodiments of the current invention, wherein FIG. 5A illustrates a perspective view, FIG. 5B illustrates a cross section view, FIG. 5C illustrates a top view, FIG. 5D illustrates a front view and FIG. 5E illustrates a side view;

FIGS. 11A-C exemplify a singled arm needle cap remover, in accordance with some embodiments of the current invention, wherein FIG. 11A illustrates a perspective view of the device, FIG. 11B illustrates a cross-section view of the device and FIG. 11C illustrates a top view of the device.

DESCRIPTION OF SPECIFIC EMBODIMENTS OF THE INVENTION

Figure 1A:
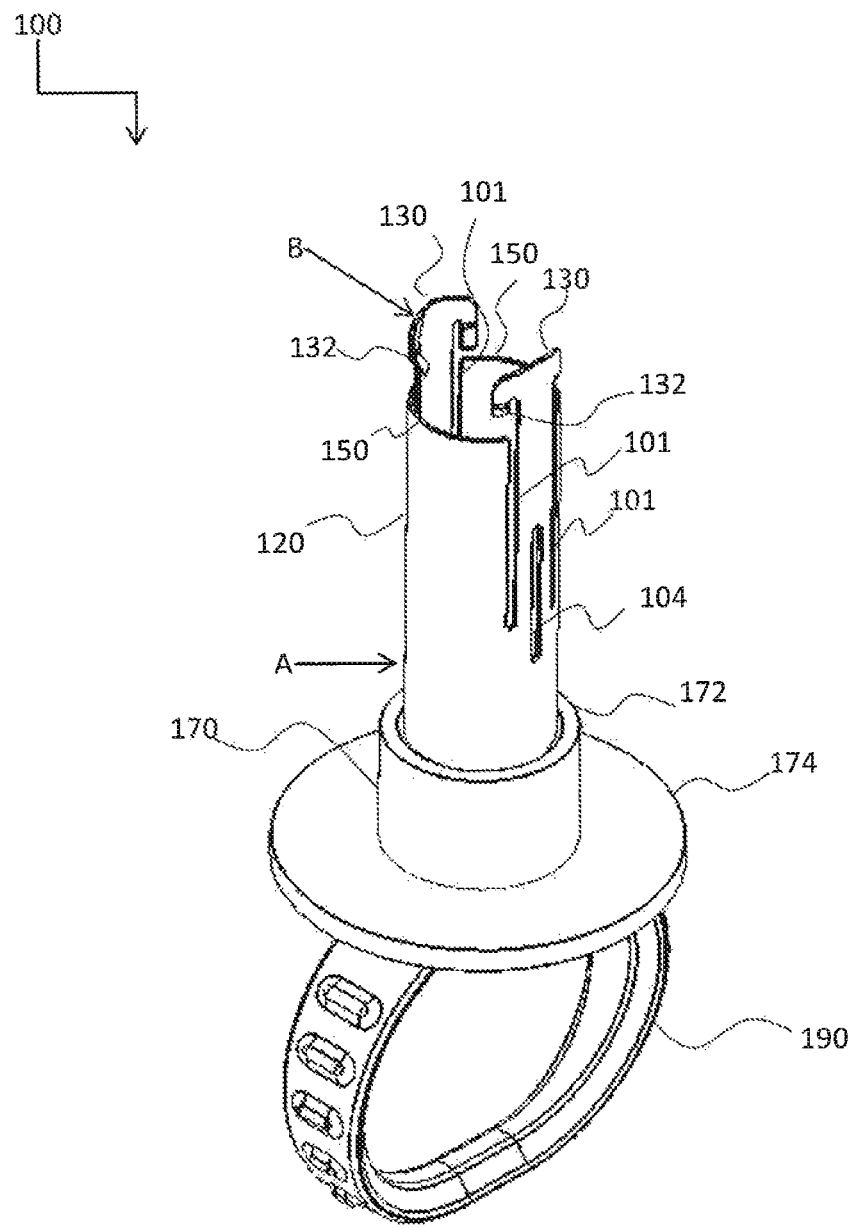
Figure 1B:
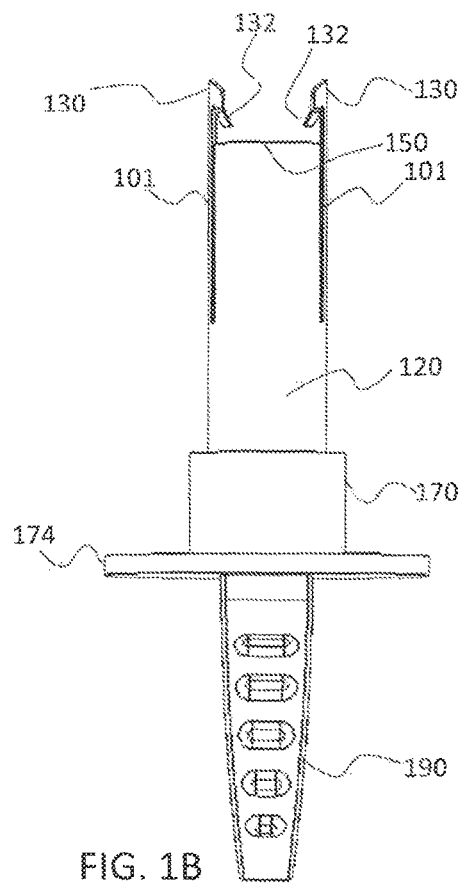
Figure 1C:
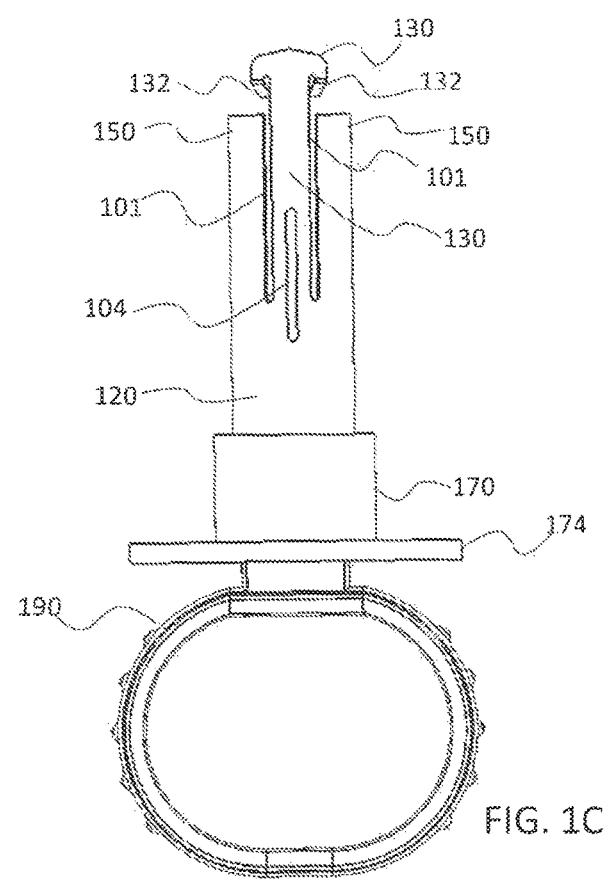
Figure 1D:
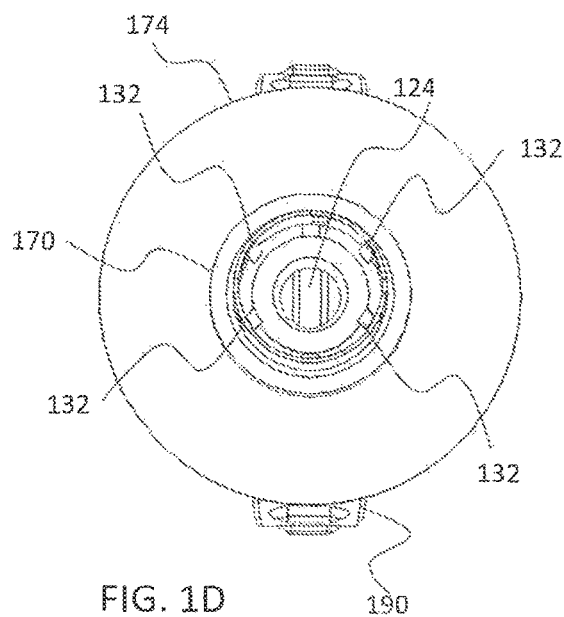
Figure 1E:
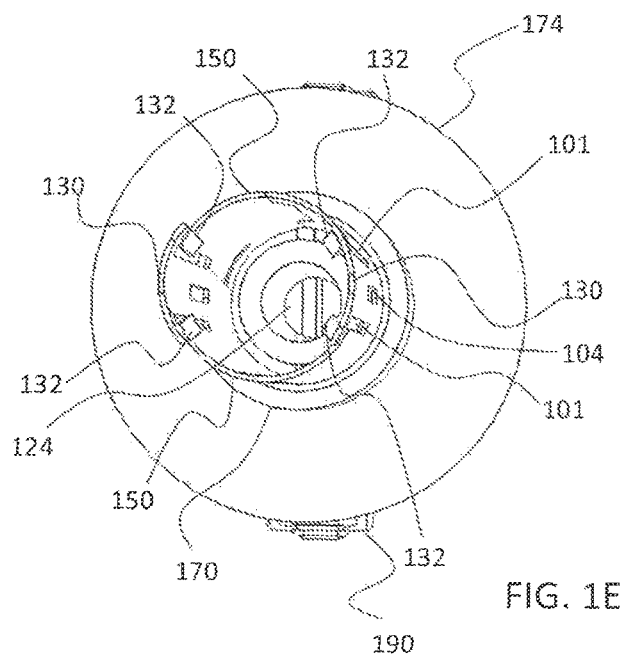

The present invention, in some embodiments thereof, relates to a needle cap remover and, more particularly, but not exclusively, to a bifurcated needle cap remover.

Overview

An aspect of several embodiments of the invention relates to a needle cap remover configured to slide in one direction and clamp in the opposite direction. In some embodiments, the needle cap remover comprises a cover body having a longitudinal axis characterized by a distal end configured to be pushed over and/or receiving and/or enveloping a needle cap, and a proximal end configured for being pulled by a user. Optionally the body is cylindrical. Alternatively, the body includes a conical section. Alternatively or additionally, the body comprises at least two longitudinal arms at least partially coupled to define a tubular structure, optionally having a diameter larger than a diameter of a needle cap.

In some embodiments, the cover body comprises at least two hooks, optionally coupled to its distal end. In some embodiments, the hooks are provided at the distal portion of the longitudinal arms. Optionally, the hooks define a diameter which is smaller than the diameter of the needle cap. In some embodiments, once the cover body is pushed over the needle cap, the hooks are deflected away from the central axis of the needle cap to allow their defined diameter to fit over the larger diameter of the needle cap. In some embodiments, deflection of the hooks is provided by elastic elements, optionally the elastic elements comprise the at least two longitudinal arms.

In some embodiments, the at least two longitudinal arms are defined by bifurcated sections in the cover body. Optionally, the bifurcated sections are configured to distribute pushing forces, potentially enabling assembly of the needle cap remover onto the needle cap without exerting too much force onto the needle cap, for example exerting no more than 100 g force, or exerting no more than 150 g force, or exerting no more than 200 g force, or exerting no more than 250 g force. Alternatively or additionally, the bifurcated sections are configured to distribute pulling forces such that potentially removing the needle cap with the needle cap remover substantially maintains an axial direction. In some embodiments, in order to pull the needle cap no more than 0.5 Kg force is applied. Alternatively, no more than 0.7 Kg force is applied. Alternatively, no more than 0.9 Kg force is applied. Alternatively, no more than 1 Kg force is applied. Alternatively, no more than 1.2 Kg force is applied. Alternatively, no more than 1.5 Kg force is applied. In some embodiments, the cap remover cover body has an integral proximal end and a bifurcated distal end.

In some embodiments, the bifurcated end of the cap remover comprises 4 slits which divide the bifurcated end into 4 longitudinal arms. Alternatively or additionally, the bifurcated end of the cap remover comprises 5, or 6, or 7, or 8 slits. Alternatively or additionally, the bifurcated end of the cap remover comprises 2, or 3 slits. Optionally, the slits are offset with respect to the longitudinal axis of the cover body, for example, tilted by an angle range of 1°-20°. Alternatively, at least some of the slits are tilted by an angle range of 15°-35°. Alternatively at least some of the slits are tilted by an angle range of 30°-45°, or any range smaller, larger or intermediate. Optionally, the slits define a triangular portion.

In some embodiments, the bifurcations are arranged symmetrically around a perimeter of the cap remover. Optionally, the bifurcations are arranged equidistantly. Alternatively, the bifurcations are arranged such that at least two different sizes of bifurcated portions, optionally in the form of elongated arms, are provided. Optionally, pairs of equally sized bifurcated portions are arranged substantially diametrically.

In some embodiments, bifurcation portions are geometrically distributed in a configuration requiring a relatively small force when pushing the cap remover onto a needle cap and a relatively large force when pulling the cap with the cap remover. Potentially, the relative location of the slits affects the directionality of the forces which are exerted on the cap remover. Alternatively or additionally, the elasticity of at least a portion of the bifurcated portions affects the directionality of the forces exerted on the cover body. In some embodiments, elasticity of the cap remover portions is affected by the perimeter length taken up by the portions. Alternatively or additionally, elasticity of the cap remover portions is affected by the composition of the portions material.

In some embodiments, the distal portion of the longitudinal arms is coupled to at least two hooks, and/or fingers. Optionally, the hooks cause the perimeter of the cap remover to be smaller than the perimeter of the needle cap. In some embodiments, when the cover body is pushed over the needle cap, once the hooks pass the top sill of the needle cap, the smaller perimeter allows the hooks to overhang the top sill. In some embodiments, at least some of the bifurcated portions, optionally in the form of longitudinal arms, are elastic enough to deflect away from the longitudinal axis of the cap remover at least to an extent which allows the smaller perimeter defined by the hooks to fit over the larger perimeter of the needle cap.

Optionally, the hooks operate at a snap-fit mechanism. In some embodiments, at least some of the hooks include projections extending towards a central axis of the cap remover. In some embodiments, when the cap remover is pushed over the needle cap, once the hooks pass over the top sill of the needle cap, the hooks and/or elastic arms bounce back and/or snap towards the central longitudinal axis. In some embodiments, when a pulling force is applied to a cover body assembled onto a needle cap, the hooks are configured to exert force in an axial direction towards to the bottom portion of the needle cap. Optionally, hooks in the form of inward projections include projections which are tilted towards the bottom portion of the needle cap, potentially creating a resisting clasp when the cover body is pulled and the projections are pushed against the top sill of the needle cap. Alternatively or additionally, snap projections are perpendicular to the longitudinal axis of the cover body.

In some embodiments, the position of the slits affects the resistance exerted by the snaps which are being pushed on to the needle cap, optionally leading to the pulling of the needle cap with the cap remover when pulling the cap remover. Alternatively or additionally, the size of the slits affects the snaps being held. In some embodiments, the position configuration of the slits allow the elastic portions to deflect away from the central axis of the cap remover when pushed over the needle cap in one direction, but at the same time cause the snaps to hold onto the needle cap when the cap remover is pulled in the opposite direction, and prevent the elastic portions from deflecting. In some embodiments, intermediate slits are provided, optionally in the elastic portions, optionally positioned in proximity to the middle portion of the longitudinal axis of the cap remover. In some embodiments, intermediate slits do not reach the edge of the cap remover body.

In some embodiments, the bifurcated portions are optionally symmetrically arranged around the perimeter of the cap remover. Alternatively or additionally, the bifurcated portions are symmetrically arranged with respect to a central axis. In some embodiments, four slits are provided, partitioning the cap remover body distal end into four portions, optionally two elastic portions and two rigid portions. Elastic portions are for example arms which can deflect away from the central axis of the cover body to at least allow coupled hooks to be fit over the perimeter of the needle cap. Rigid portions are for example portions of the cover body which are not configured to deflect away from a central axis of the cover body. In some embodiments, elastic portions are positioned substantially diametrically. Alternatively or additionally, rigid portions are positioned substantially diametrically.

In some embodiments, the elastic portions take up a smaller perimeter length with respect to the rigid portions. For example, the elastic portions comprise 10-40% of the body cover perimeter, while the rigid portions comprise 90-60% of the body cover perimeter. Alternatively, the elastic portions comprise 20-30% of the body cover perimeter, while the rigid portions comprise 80-70% of the body cover perimeter. It is a potential advantage to provide larger rigid portions and smaller elastic portions, as it contributes to the rigid and elastic characteristics of the portions, respectively.

In some embodiments, a connector, for example a body containing a clamping mechanism, is provided to be assembled onto the cap remover cover body, optionally to connect the cover body to other features. Alternatively or additionally, the connector acts as a securing mechanism and is optionally shaped and sized to add mechanical stability to the cover body. In some embodiments, the cover body is positioned within an injector system and the connector can be operated from the outside of the injector system. In some embodiments, the cap remover comprises fasteners configured to interlock with the connector. Potentially, the fasteners prevent lateral movement of the cover body with respect to the needle cap. Optionally, the connector further comprises a user handle. In some embodiments, the fasteners interlocking with the connector limit force exertion in a rotational direction, potentially precluding sliding of the needle remover body around the needle cap and/or preserving an orientation of the needle cap remover with respect to the needle cap.

An aspect of several embodiments of the invention relates to a medicament delivery system, for example an autoinjector comprising a needle cap remover. In some embodiments, a needle is installed into an autoinjector and is covered with a needle cap. Subsequently, an adhesive liner is installed to the injector. In some embodiments, removal of the needle cap also brings about removal of the adhesive liner. In some embodiments, the needle cap remover is positioned perpendicularly to the base of the injector system, to allow a user a more intuitive pulling direction.

An aspect of several embodiments of the invention relates to a needle cap remover having at least two separate fastening mechanisms. In some embodiments, a first fastening mechanism comprises at least two enveloping arms sized and shaped to envelop at least a portion of a needle cap. In some embodiments, the arms are coupled in at least a portion across their longitudinal axis, optionally enabling the arms to hinge-tilt from the coupled position. Optionally, when the distal portions of the arms tilted away from the longitudinal axis of the cap remover, the arms define an open configuration, and when the arms are not tilted away they define a closed enveloping configuration. In some embodiments, a second fastening mechanism is configured to latch the arms in their closed configuration, optionally in the form of a connector which may also connect arms being inside an injector system to an outside of the injector system.

In some embodiments, a closed configuration is defined by having the members enclosed around the needle cap. An opened configuration is defined by having the members spaced to have a diameter greater than the needle cap, optionally, at least as wide as the widest diameter of the needle cap. In some embodiments, the arms are provided with fingers that are configured to overhang a top sill of the needle cap once the arms are in their closed configurations. Optionally, when the cap remover is being pulled, the connector keeps the arms in their closed configuration and the fingers push down on the cap and remove it from the needle, optionally in substantially a downwards axial direction.

An aspect of some embodiments of the invention relates to a device protective cover allowing access of a needle cap remover into an inner portion of the device, and designed to be assembled onto the needle cap remover and its user pulling handle after the remover is assembled with its user handle. In some embodiments, the protective cover comprises a plurality of layers, optionally at least an adhesive layer and a liner layer protecting the adhesive surface of the adhesive layer. In some embodiments, protective cover is designed to be removed by pulling the needle cap remover through its user handle in a linear direction. Optionally, only a portion of the protective cover area is attached to the injector, while an extending edge extends from the end of the portion attached. In some embodiments, the extended edge is folded and/or bent to be oriented facing the attached portion, optionally by handing the extended edge onto the user handle.

In some embodiments, the protective cover comprises at least two apertures. Optionally, a first aperture allows insertion of the needle cap remover into the injector inner portion. In some embodiments, the first aperture is sized to match the circumferential shape of the needle cap remover, optionally being wider than the needle cap remover. It is a potential advantage to keep the first aperture small enough to allow sufficient stability when the device is adhered to the patient and the needle is penetrating through this aperture. It is another potential advantage to design the aperture to have a width smaller than a human finger, to prevent a user from inserting his figure into the needle region, e.g. smaller than 15 mm, and/or smaller than 10 mm, and/or smaller than 5 mm. In some embodiments, the cap remover body has no outward protrusions in the region which needs to be inserted into the aperture, in order to preserve the option for a small aperture width as allowed by the body's own width.

Also optionally, a second aperture allows fitting over the user handle. In some embodiments, a user handle is provided as having a long dimension and a short dimension. Optionally, the second aperture is sized as an elongated slit, having a length being longer than the long dimension and shorter than the short dimension of the handle. In some embodiments, the elongated aperture is assembled onto the handle by first orienting the aperture to face the shorter dimension and then rotating the edge of the cover such that the elongated aperture slides towards the longer dimension, optionally eventually being oriented to face the long dimension. In some embodiments, when placing the liner over the handle, no force is applied to the cap remover and/or needle cap. Alternatively, a force smaller than 50 g, and/or 100 g, and/or 150 g is applied.

In some embodiments, the edge is stabilized in place by the handle becoming wider as the aperture slides toward the long dimension and by constraining the edge of the aperture against the wide portion of the handle, being wider than the aperture. Alternatively, the edge is directed to pass the widest portion of the handle and reach a narrower portion, causing the aperture edge to overhang over the wide portion serving as a shoulder portion. Alternatively or additionally, the handle is rotated after the edge is passed over it, such that the long dimension of the handle is found at an angle to the length of the aperture, thereby preventing a slide of the edge in the direction it passed over. Alternatively or additionally, the edge slides to an offset direction from the center of the long dimension, misaligning the aperture with the handle's long dimension.

In some embodiments, at least a portion of an edge of at least one of the apertures also comprises a supporting layer in the form of a rigid layer, rigid enough to provide mechanical stability to prevent bending at the forces which are applied when pulling the cover. Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

EXEMPLARY EMBODIMENTS

1 An Exemplary Needle Cap Remover

Referring now to the drawings, FIGS. 1A-E illustrate a needle cap remover 100 designed to remove a needle cover in accordance with an embodiment of the current invention. In some embodiments, needle cap remover 100 is designed such that forces exerted on the needle cover do not disturb a sterility state of a needle cap enveloping a sterile needle.

In some embodiments, needle cap remover 100 has an elongated cover body 120 configured for at least partially covering a needle cap. Elongated body 120 in some embodiments is sized and shaped to envelope a needle cap, optionally tightly. Elongated body 120 optionally includes a bore 124. For example, body 120 and/or bore 124 may be cylindrical. Alternatively, a portion of body 120 and/or bore 124 may be conical for example being tapered and/or having the shape of a conical section and/or funnel shaped. Body 120 has a distal end B which in some embodiments is found in proximity to a top portion of a needle cap, i.e. the portion having the needle receiving bore. Body 120 has a proximal end A, which in some embodiments is found in proximity to a bottom portion of a needle cap, i.e. the portion closest to the needle tip.

In some embodiments, elongated body 120 comprises at least two bifurcations, optionally dividing body 120 into at least two portions, potentially portion 130 and/or portion 150. In some embodiments, at least a first 130 of the at least two portions has elastic properties, optionally, the two portions are in the form of longitudinal arms. Alternatively or additionally, at least a second 150 of the at least two portions has rigid properties, e.g. is more rigid than first 130 portion. In some embodiments, elastic portions 130 are elastic enough to deflect away from a central axis of the cover body by an angle having a range of 1°-5°. Alternatively, elasticity is enough to enable deflection by an angle having a range of 10°-15°. Alternatively, elasticity is enough to enable deflection by an angle having a range of 15°-20°. In some embodiments, reaching an angle greater than the elasticity range results in plastic deformation of the arms, optionally, reducing the resilient snapping of the arms to their original position. Alternatively, deflection beyond the higher threshold of the range results in breakage of the arms.

In some embodiments, elasticity and/or rigidity is affected by the size, shape and/or position of slits 101 created by the bifurcations, optionally their longitudinal length and/or position along the longitudinal axis of body 120. Alternatively or additionally, the width of slits 101 influences the elasticity of its adjacent portions. An optional range for the longitudinal length of slits 101 is between about 5 mm and about 20 mm. Alternatively, a length of slits 101 is between 7 mm and 10 mm. An optional range for the width of slits 101 is between 0.3 mm and 3 mm. Optionally, the width of slits 101 is 2 mm.

Alternatively or additionally, elasticity and/or rigidity are determined by the position of slits 101 around the perimeter of body 120 and thus according to the perimeter length taken up by elastic portion 130 and/or the perimeter length taken up by rigid portion 150, which are defined by the positions of slits 101. In some embodiments, slits 101 define the partition of the distal portion of body 120 into relatively elastic 130 and relatively rigid 150 portions. Optionally, portions 130 are elastic relative to portions 150, and portions 150 are rigid relative to portions 130. In some embodiments, elastic portions take up to 50% of the perimeter of body 120. Alternatively, elastic portions take up to 40% of the perimeter of body 120. Alternatively, elastic portions take up to 30% of the perimeter of body 120. Alternatively, elastic portions take up to 20% of the perimeter of body 120. Alternatively, elastic portions take up to 10% of the perimeter of body 120.

In some embodiments, at least one intermediate slit 104 is provided, optionally in elastic portion 130, potentially increasing its elasticity. Optionally, intermediate slit 104 is surrounded by body 120 and does not continue all the way to the edge of 120. In some embodiments, intermediate slit 104 is positioned centrally between two of slits 101. Alternatively or additionally, intermediate slit 104 is positioned asymmetrically with respect to slits 101, potentially leading to a favorable direction in reaction to force exertion on device 100. Alternatively or additionally, intermediate slit 104 is positioned in proximity to only one of slits 101. Optionally, intermediate slit 104 has identical dimensions to slits 101. Alternatively, intermediate slit has smaller or larger length. Alternatively or additionally, intermediate slit has smaller or larger width.

In some embodiments, elastic portion 130 and rigid portion 150 have distinct lengths. Optionally, elastic portion 130 extends beyond rigid portion 150 towards the distal end of device 100. In some embodiments, at least some of the elastic portions comprise snaps 132 at their distal end. Snaps 132 are configured in some embodiments to snap body 120 onto the needle cap's top portion. Optionally, snaps 132 create a perimeter which is smaller than the perimeter of the needle cap. In some embodiments, due to the elasticity of elastic portions 130, when device 100 is pushed onto the needle cap, elastic portions 130 are directed away from the central axis of body 120. Optionally, once snaps 132 pass the top portion of a needle cap, they snap into their original position, essentially clasping the needle cover 100 over the needle cap and/or clasping over the top of the needle cover and/or over a top sill of the needle cover. Optionally snaps 132 are angled inward and/or wedged into the top and/or a top sill of the needle cap, being tilted with respect to the central longitudinal axis of the needle cap. In some embodiments, the snaps are deflected towards the central longitudinal axis of the needle cap. Optionally the angle of snaps 132 pulls the distal portion of elastic portion 130 inward (e.g. towards the central axis of the cap) when the cap remover is used to pull the cap.

In some embodiments, needle cover 100 further comprises a user handle 190, optionally in the form of a ring as illustrated in FIG. 1. Optionally, user handle 190 is interconnected to cover body 120 by a connector, optionally having connector body 170 for connecting to cover 120 and connector base 174 potentially enabling easier gripping of cap remover 100. In some embodiments, connector body is a separate feature which is connected to body 120, optionally through connector ring 172, further optionally including fastening means 410 configured to interlock ring 172 and body 120, for example as shown in FIGS. 4 and 5. Alternatively, connector base 170 is provided as a continuation of body 120, without being a separate feature. Optionally, fasteners 410 are configured to interlock the body cover with the connector such that a lateral movement of the cover body 120 with respect to its enveloped needle cap is inhibited.

In some embodiments, cover body 120 comprises a recess 420, optionally configured to complement protruding longitudinal guides in the needle cap, thereby guiding the direction of inserting the cover body over the needle cap. In some embodiments, at least 2 recesses 420 are provided. Alternatively, at least 3 recesses are provided. In some embodiments, recesses are provided in the proximal portion of the cover body.

Optionally, connector base 170 and/or body 120 comprise complementary longitudinal sections, which optionally facilitate orientation of the connector base 170 with respect to body 120 when assembling the two together. Longitudinal sections optionally include grooves. Alternatively or additionally, longitudinal sections include protrusions. In some embodiments, an inner portion of body 120 comprises complementary longitudinal sections configured to complement sections provided in a needle cap, potentially aiding in a correct orientation of body 120 with respect to the needle cap. Also potentially, complementary sections can assist in reducing the force needed to assemble cover 120 onto a needle cap.

2 Exemplary Usage of the Needle Cap Remover in an Exemplary System of a Drug Delivery Device In some embodiments, a needle cap remover is used with a drug delivery injector system. Optionally, the injector is provided to the user after the system has been pre-assembled with a medicament, contained in a cartridge having a needle. Optionally the needle is embedded within a housing of an injector system and/or not visible to the user. It is potentially desirable that the medicament and the needle are preserved in sterility until they are used or just before use. For example it is potentially beneficial, to provide the device to the user while the needle is still protected by the needle cap. Optionally the needle cap is internally embedded within the housing. A needle cap remover and/or a handle as provided in accordance with some embodiments of the invention is assembled onto the needle cap, potentially having an internal portion residing inside the housing, while having an external portion outside the housing and being available for a user to pull.

Reference is now made to FIG. 2 illustrating an exemplary drug delivery device in the form of an automatic injector, being in a secure state for example safe for transport, and having cap remover 100 at least partially embedded. In some embodiments, adhesive liner 250 covers the activation zone of the device and/or an adhesive. Optionally, adhesive liner 250 is associated with cap remover 100 such that pulling cap remover 100 also leads to peeling of adhesive liner 250. In some embodiments, cap remover 100 serves as a coupler, optionally synchronizing removal of the needle cap and unsealing of the activation zone of the device, optionally by peeling a protective cover layer.

In some embodiments, an adhesive section of an injector system is provided having two sections, a main adhesive 212 and a secondary adhesive 214, optionally adhesive 214 having a smaller contact area than adhesive 212. A potential advantage of providing at least two adhesive sections 212 and 214 is a guided removal of the device from the user's body, as an adhesive having a smaller contact area is likely to detach first.

In some embodiments, cap remover 100 and/or its associated adhesive liner 250 are associated with a battery isolator. Optionally, once cap remover 100 is pulled and/or adhesive liner 250 is peeled, battery isolator is also removed allowing to power on the injector system. In some embodiments, once power is on, the injector can no longer be turned off and/or repacked in its original state. Alternatively or additionally, once power is turned on, a mobile device is alerted. Optionally, a bar code is provided in the injector system for associating a mobile device to communicate with the injector system.

Figure 2A:
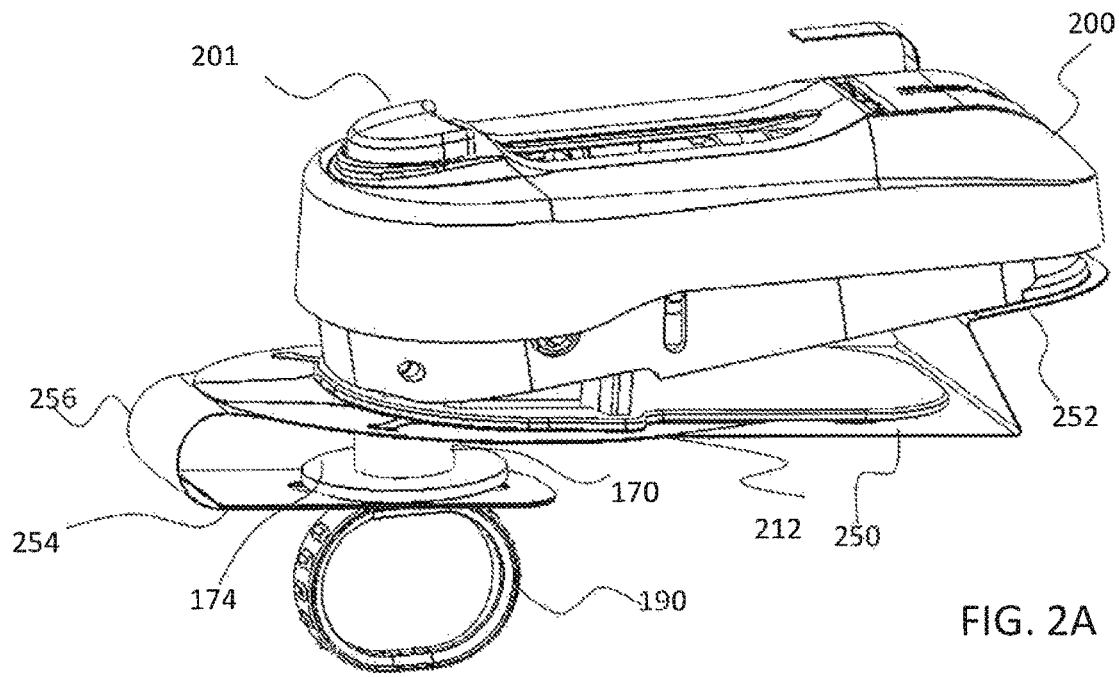

FIG. 2A illustrates an exemplary injector system having an injector housing 200 and operation button 201, and having cap remover device 100, optionally in proximity to the operation button 201. In accordance with some embodiments, the injector system comprises a two sectional adhesive 214 and 212, optionally covered by adhesive liner 250. In some embodiments, adhesive liner 250 comprises a top portion 252 for covering sections 212 and 214, optionally adhesive 212 and adhesive 250 comprise an aperture for allowing access to the needle and/or needle cap and/or needle cap remover from outside housing 200. In some embodiments, adhesive liner 250 also comprises a bottom portion 254, optionally connected to top portion 252 through bending 256. In some embodiments, bottom portion 254 is associated with needle cap remover 100, optionally by having an aperture for allowing device 100 to extend from within housing 200, through top portion 252 and through bottom portion 254. Optionally, bottom portion 254 is positioned between handle 190 and connector base 174. In some embodiments, connector base 174 comprises a plate, optionally having a diameter larger than bore 124 of body 120. Potentially, once handle 190 is pulled, connector base 174 pulls adhesive liner bottom portion 254, which through bend 256 leads to peeling top cover 252 starting from the device extreme end being closest to bend 256. In some embodiments, connector 170 comprises an orientation feature, such as for example beam 178, optionally sized and shaped to fit into housing 200, for example at slit 270, as shown in FIG. 2C. Potentially, orientation feature 178 is configured to guide the insertion of cap remover device in a specific rotational orientation. Optionally, at least one fastener 350 is provided in connector 170 and/or cover body 120, potentially setting the orientation of connector 170 with body 120.

Figure 2B:
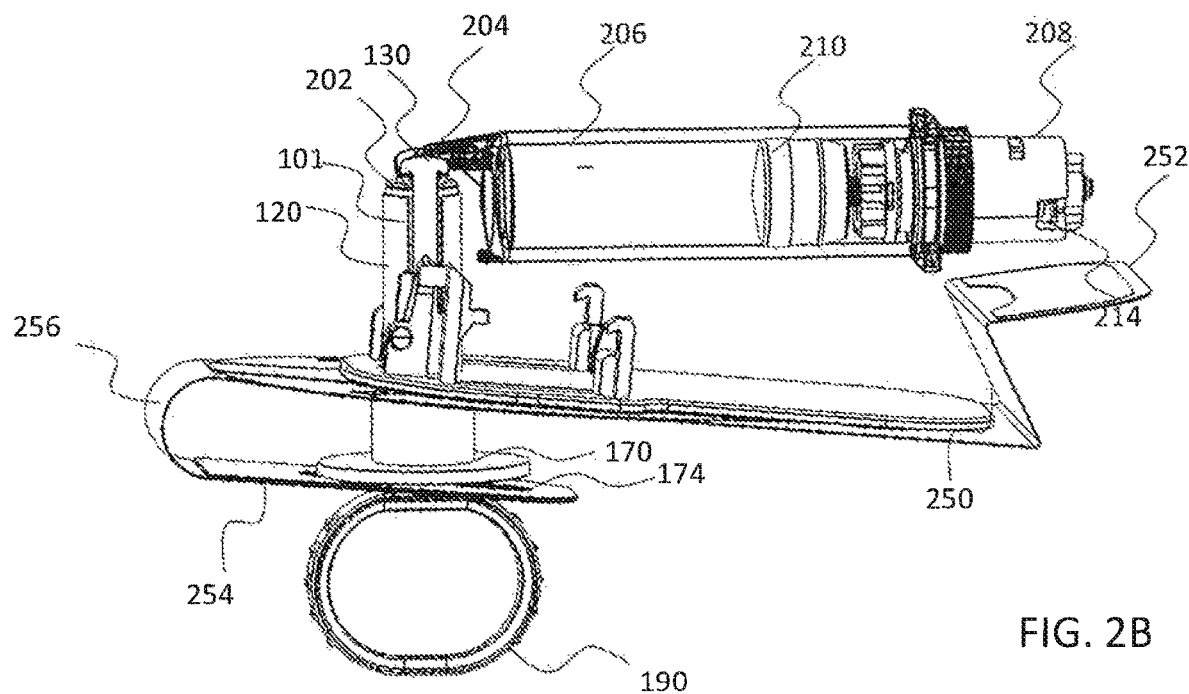
Figure 2C:
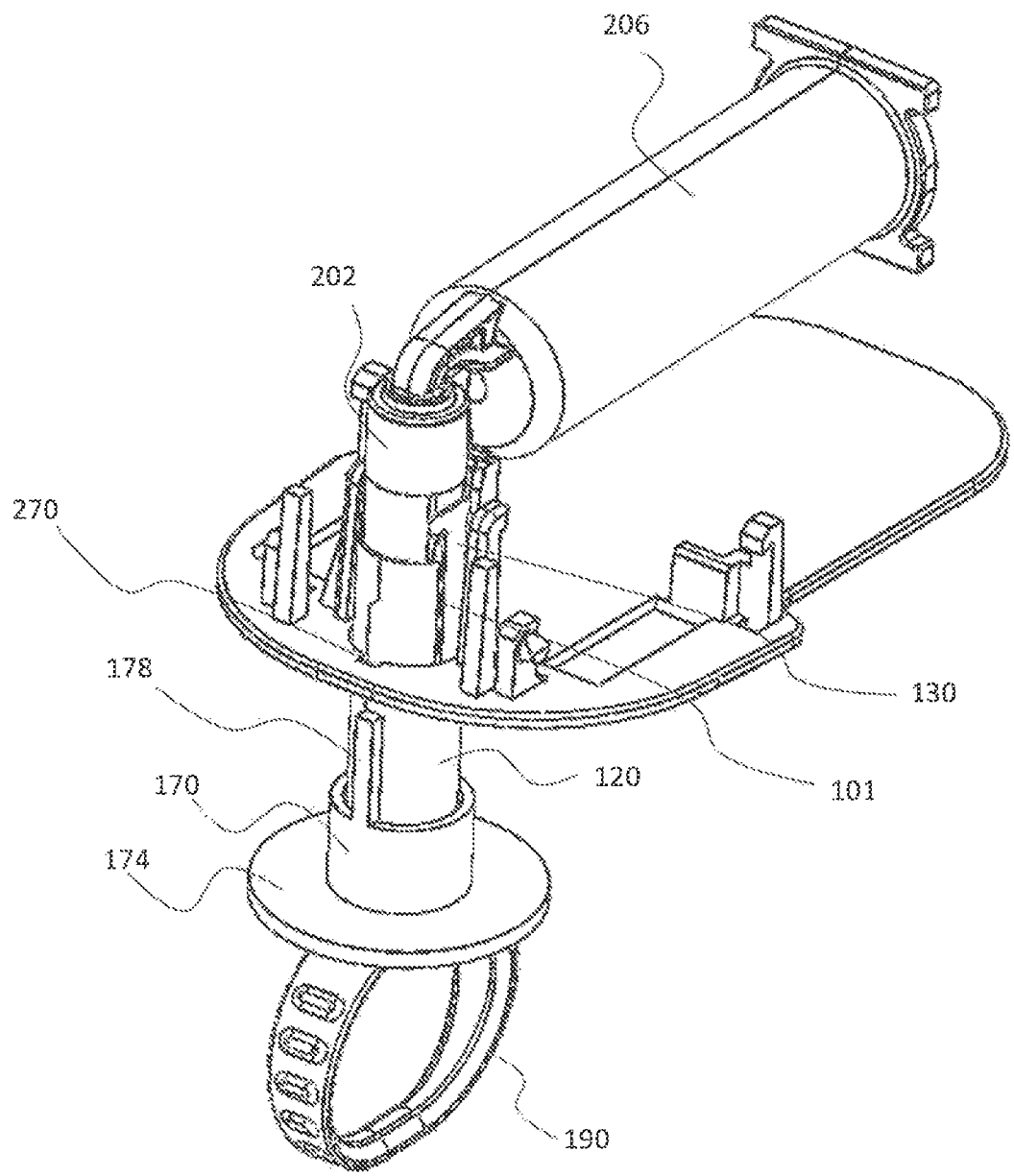

FIG. 2B illustrates an embodiment of an injector system having a needle cap 202 associated with a cannula 204 of a medicament cartridge 206, resting on a frame of housing 200 of the injector, optionally the injector system is operated automatically by means of motor 208, potentially pushing plunger 210. Putting pressure on the proximal end of the injector (which is optionally covered by front cover 250) optionally pushes needle protector 214 against the frame. Optionally putting pressure on the proximal end of the injector will not activate the injector and/or will not un-shield the needle. Needle cap 202 optionally acts at a physical shield covering the tip of a needle associated with cannula 204.

Optionally, needle cap 202 includes a rigid outer shell and a sterile rubber core. When needle cover 202 is installed over a sterilized needle, the rubber core may protect the sterility of the needle and/or the shell may protect the needle from causing a stick hazard. Alternatively or additionally, a needle is covered with a single cover (either rubber or rigid) that preserves sterility and/or prevents a stick hazard.

For example, a prefilled syringe may be installed into an autoinjector with a needle already covered with needle cover 202. Before shipping the injector, adhesive liner 250 may be installed onto the injector. In some embodiments, a needle cap remover 100 is pushed over cap 202, optionally additionally serving as a needle cap protector. Cap remover 100 in some embodiments includes clasps (for example snaps 132) which engage cap 202. When needle cap remover 100 is removed from the injector, clasps 132 may pull off needle cap 202.

3 A Needle Cap Remover Including an Adhesive Liner

Reference is now made to FIG. 3, illustrating perspective and side views of a needle cap remover optionally having a cover 120, and/or adhesive liner 250 and/or handle 190.

Figure 3A:
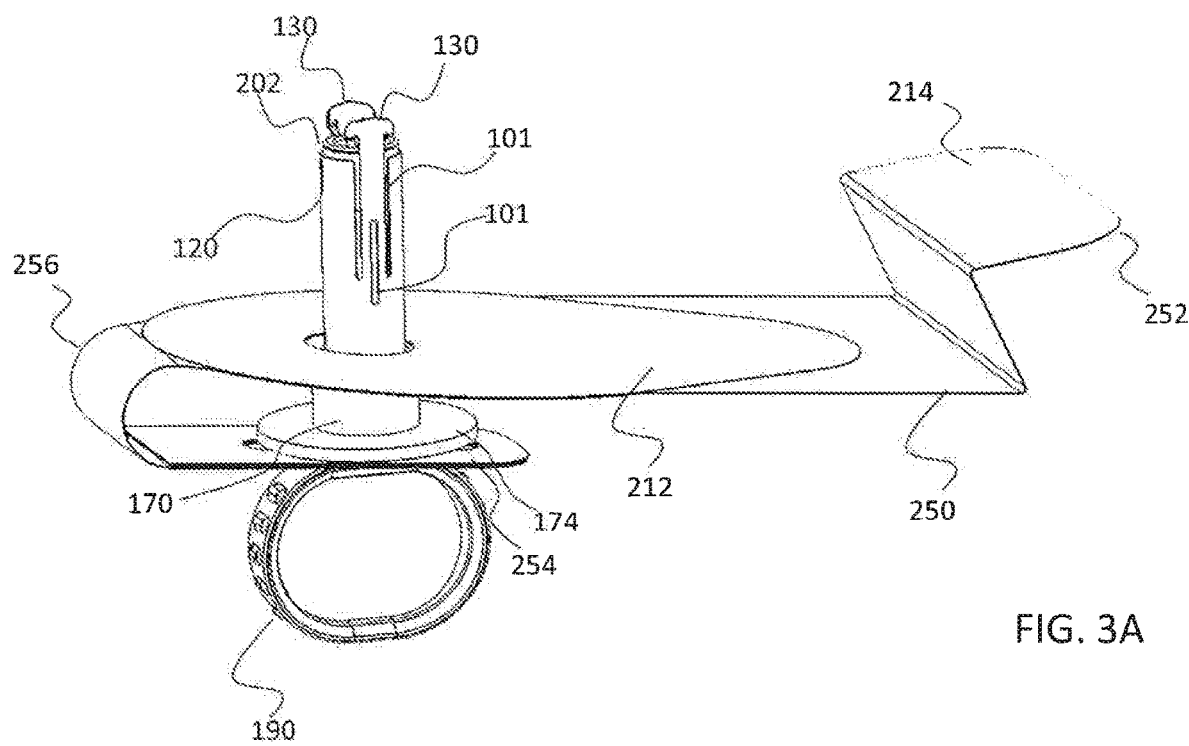
Figure 3B:
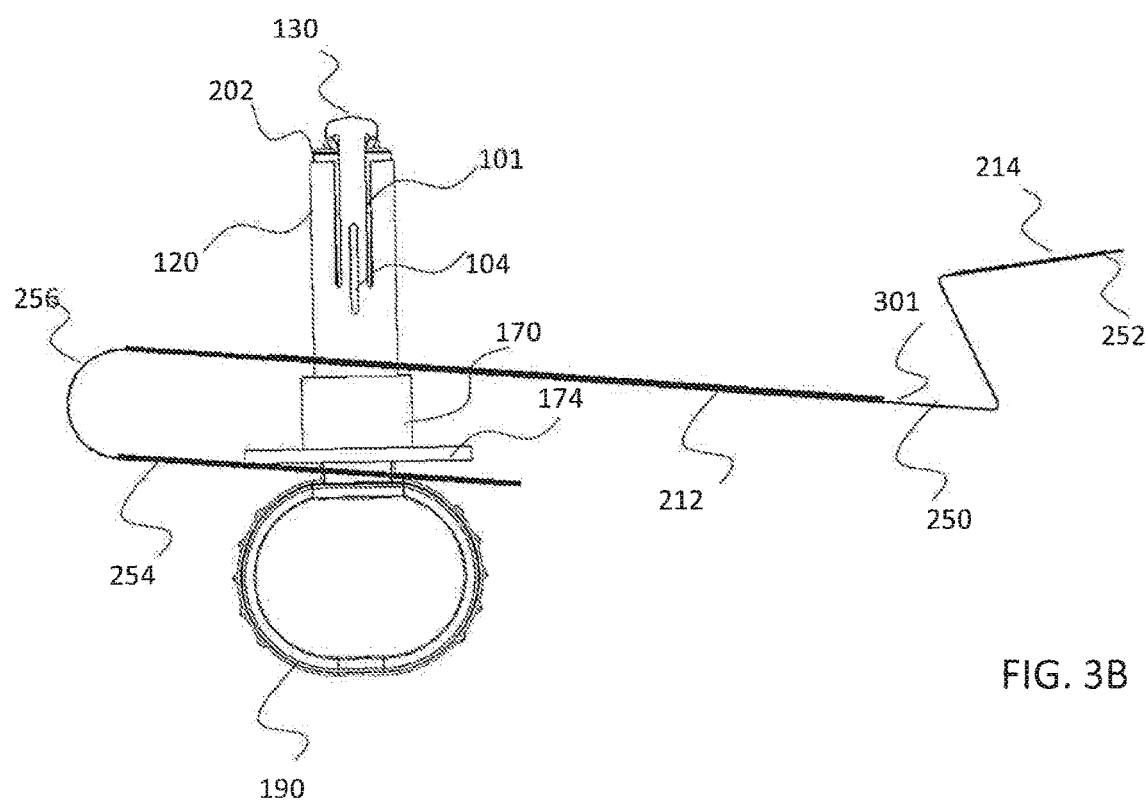

FIGS. 3A and 3B illustrate an injector needle cap remover and adhesive liner in accordance with an exemplary embodiment of the present invention. The cap remover includes for example a handle 190 and/or a needle cap cover 120 and/or an adhesive liner 250 for covering an adhesive 212/214 and/or for covering an activation zone of the injector system. Handle 190 and/or cover 120 and/or cover 250 are optionally connected to a battery insulator. Removing the cover optionally places the injector into an enabled state.

In some embodiments needle cap remover 100 serves as a peeler for an adhesive liner 250. For example, cap remover 100 is optionally hinged and/or flexible. Optionally, handle 190 is located at the center of cap remover 100. In some embodiments, handle 190 does not pull an adhesive liner 250 away from the whole surface of the adhesive 214/212 all at once (an act that would potentially require a large force to overcome the sticking force over a large surface). When handle 190 is pulled, the center portion of cap remover 100 optionally moves away together with adhesive liner bottom portion 254. For example cover 254 is optionally is pulled away in such a way as to peel adhesive liner bend 256 following by peeling of top portion 254 bit by bit. Peeling is optionally from an extreme edge of main adhesive 212 and/or optionally peeled towards the opposite end, finally removing top portion 252 from secondary adhesive 214.

In some embodiments, adhesive 212 is provided onto a hinged plate 301. Optionally, once needle cap remover 100 and cover 250 are removed, a user can attach the device onto an injection site and optionally collapse hinged plate 301 to be parallel to the device. In some embodiments, a sensor senses the orientation of the hinged plate 301 with respect to the device, only allowing operation when the two are aligned. Alternatively or additionally, once plate 301 is parallel, a mechanical mechanism allows for operating the injection, such as for example, by tilting a blocking feature, such as an internal plate.

Figure 3C:
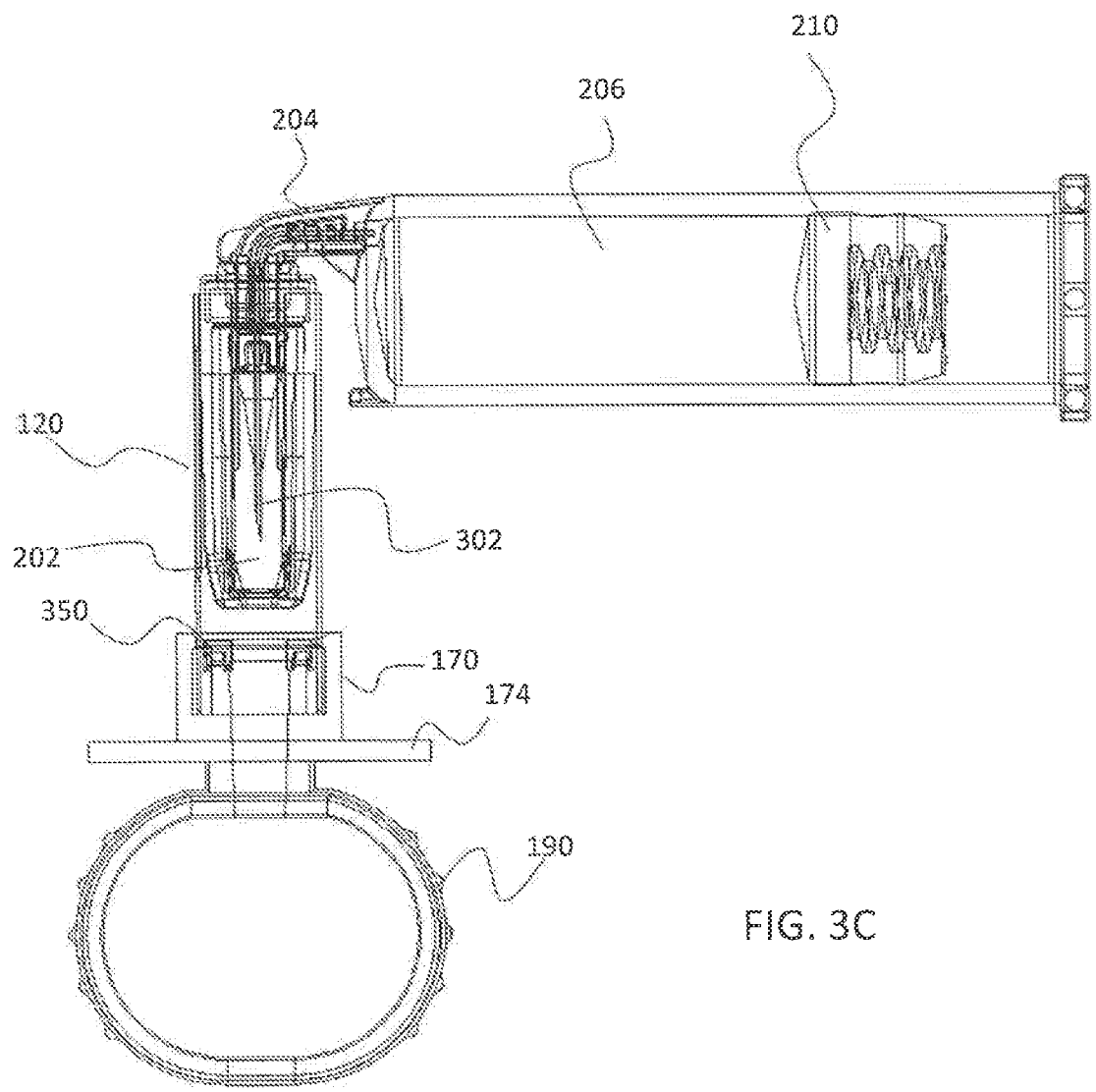
Figure 3D:
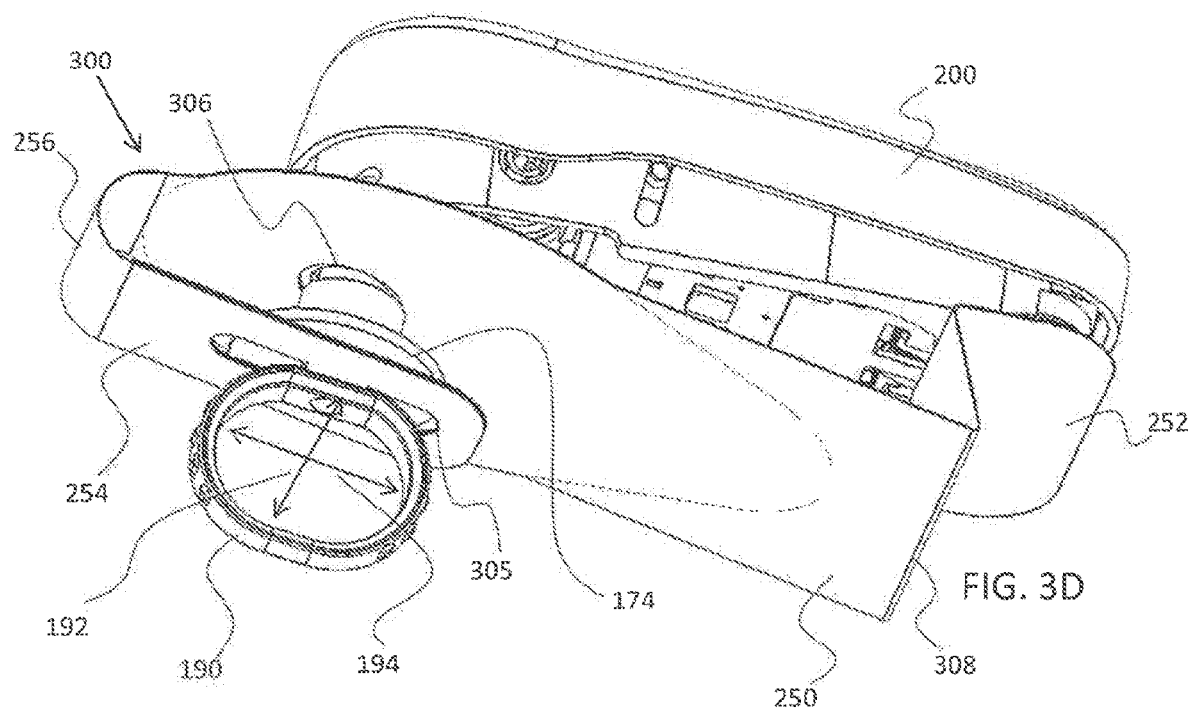
Figure 3E:
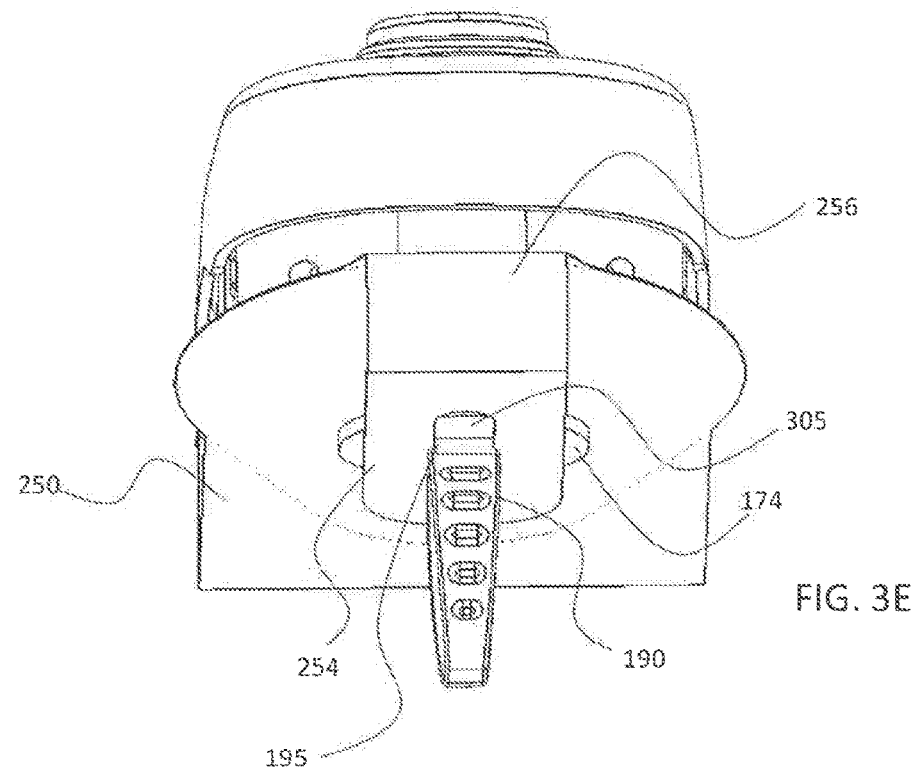
Figure 3F:
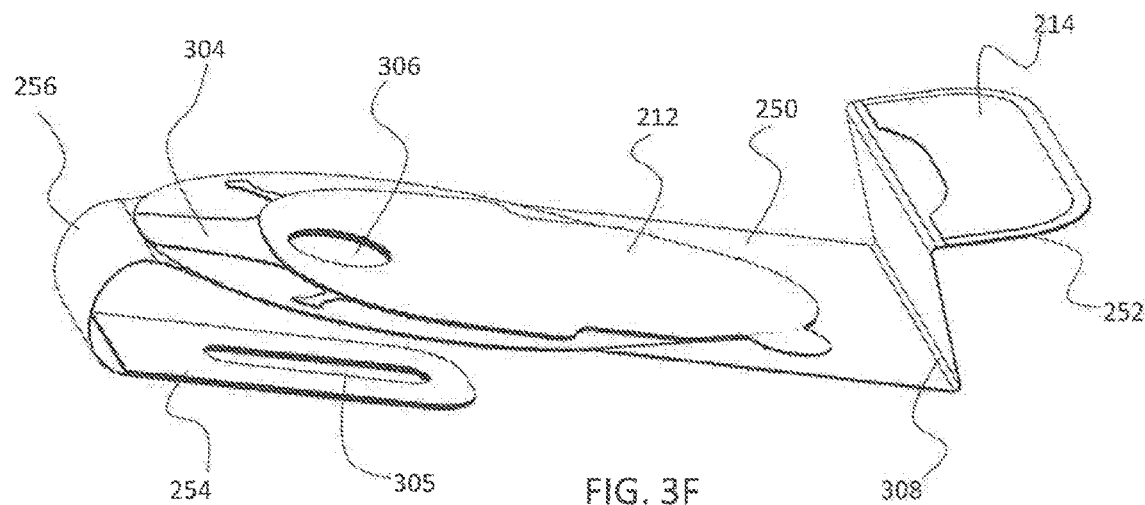

Reference is now made to FIG. 3C, illustrating a cross section of a side view of a cap remover device assembled onto a needle cap shielding a needle of an injector system, in accordance with some embodiments of the invention. In some embodiments, cover body 120 is configured to be pushed over needle cap 202 which shields a sterility state of needle 302. Optionally, pushing body 120 over cap 202 does not disturb the sterility state of the needle. In some embodiments, cover body 120 comprises a tubular shape, optionally conical. Alternatively, the tubular shape is cylindrical. Alternatively, only a portion of cover body 120 is defined as tubular, and this portion potentially couples at least two arms provided by the cover body 120. Alternatively, cover body is bifurcated to define at least two arms, optionally elastic.

In some embodiments, the elastic portions of cover body 120 allow it to be pushed over cap 202 in spite of having elements defining a smaller perimeter than the largest perimeter of cap 202.

Reference is now made to FIGS. 3D-3G, illustrating exemplary embodiments of a device cover, optionally protecting adhesive properties which are possibly used to couple the device base to a patient's body.

In some embodiments, housing 200 includes in its base a device cover 300. In some embodiments, cover 300 comprises at least two layers, one being an adhesive layer and the other being a liner for protecting the adhesive surface of the adhesive layer. In some embodiments, an adhesive surface of cover 300 assist a user to hold an injector steady on the skin of a patient for an extended period. Optionally, the adhesive surface is intermittent throughout the surface of cover 300. In some embodiments, cover 300 is partitioned at point 308, dividing the adhesive surfaces of the device between main section 250 and secondary section 252, optionally section 252 having a smaller surface area, potentially leading a user in the direction the device is removed, due to the ease of extracting the smaller adhered area with respect to the larger adhered area. In some embodiments, folding consists of bending and/or arching, and/or curving and/or winding and/or twisting. Optionally, section 250 and/or section 254 have circular shapes. Alternatively or additionally they may have a shape other than circular, for example oval, rectangular and/or irregular.

In some embodiments, cover 300 comprises at least one portion for connecting to a base of housing 200. In some embodiments, cover 300 comprises an extension 254 extending beyond a surface area of the housing base. Optionally, extension 254 is folded over at section 256 to be positioned to face portion 250 of cover 300.

In some embodiments, cover 300 comprises at least two apertures 305 and 306. In some embodiments, a first aperture 306 comprises in section 250 is sized and shaped to allow insertion of needle cap remover body 120 through it and into the inner portion of the injector device, which comprises the needle. Optionally, aperture 306 extends through the adhesive liner and the protective liner, and any other layer comprised the protective cover 300. In some embodiments, aperture 306 comprises a circumference shape matching a circumference shape of the needle cap remover body 120 and optionally, having a width being no more than about 1 mm, or about 0.7 mm, or about 0.5 mm, or about 0.3 mm wider than the width of the remover body 120.

Optionally, the adhesive liner is folded over at point 256, forming an extension 254 which directs a linear unsealing force into a guided peeling force starting from the folded edge. In some embodiments, a second aperture is provided in extension 254 of cover 300 which extends from the cover portions being connected to the device base, such as section 250 and/or 252, through bent portion 256. Optionally, the second aperture 305 is used to assemble section 254 onto the connector of needle cap remover body 120. In some embodiments, needle cap remover device serves as a coupler, coupling the needle cap at its distal side and the user handle 190 at its proximal side, optionally through connector 170. In some embodiments, the user handle comprises a protruding element opposite said coupler, e.g. being proximal to the proximal end of the needle cap remover 100.

In some embodiments, second aperture 305 comprises an elongated orifice. In some embodiments, the elongated orifice is sized to be pulled over a user handle 190 extending from needle cap remover body 120, optionally connected to it through connector 170. Optionally, user handle 190 comprises a protruding element having a long dimension 194 and a short dimension 192. In some embodiments, elongated orifice 305 has a length which is longer than short dimension 192 and longer than long dimension 194. In some embodiments, user handle 190 has a widening portion towards its connection with the connector 170, optionally ending in shoulder 195, shown in FIG. 3E. In some embodiments, a width of orifice 305 is shorter than a width defined by shoulder 195. In some embodiments, orifice 305 is at least partially made of a material which is elastic and/or resilient enough to allow pushing the orifice over the shoulder, despite its shorter width. Optionally, extension 254 is held over handle 190 by overhanging shoulder 195. Alternatively or additionally, shoulders 195 include the widest portion of the narrow portion of handle 190, sized to be not smaller than a width of orifice 305. Optionally, orifice 305 is stabilized onto shoulders by friction.

In some embodiments, an additional supporting layer is engaged with the protective cover, optionally being intermittent and not continuous over an area of cover 300. In some embodiments, supporting layer is made of a material being rigid enough to increase a rigidity of the protective liner, potentially providing mechanical strength for cover 300. Optionally, supporting layer is provided at least in the sections comprising apertures 305 and 306. In some embodiments, supporting layer is not found in extension 256.

In some embodiments, an injector housing is provided with cover 300 being at least partially connected to its base, optionally by an adhesive layer. Optionally, the injector is assembled by interlocking a cartridge having a capped needle within an inner portion of housing 200, such that the cartridge central axis is perpendicular to the cover, and the capped needle is centrally aligned with aperture 306. In some embodiments, a distal end of needle cap remover is inserted into the inner portion of the base of housing 200 through aperture 306, and is pushed over the capped needle. Optionally, the proximal end of cover body 120 remains protruding externally to housing 200.

In some embodiments, a user handle is connected to the proximal portion of body 120, optionally through connector 170. In some embodiments, user handle 190 is characterized by a protruding element extending outwardly from the base and having a short dimension 194 and a long dimension 192. In some embodiments, extension 254 is folded over the user handle 190 by first orienting aperture 305 to face the shorter dimension 194 of handle 190, followed by rotating the cover extension 254 over the handle until the aperture 305 is oriented to face the longer dimension 192.

In some embodiments, aperture 306 and 305 are centrally aligned. Alternatively or additionally, aperture 305 slides across along the long dimension 192 of handle 190, such that a longitudinal axis is not centrally aligned with aperture 306 and/or with handle 190. Potentially, sliding aperture 305 with respect to handle 190 further stabilizes its position and prevents rotation of the aperture 305 in the reverse direction. Optionally, slide of aperture 305 with respect to handle 190 is produced with extension 256 is stretched between section 250 and extension 254.

In some embodiments, handle 190 comprises a widening portion extending in a direction from a proximal end defined as being away from housing 200 and widening when approaching a distal end of the handle defined as being proximal to housing 200, optionally being widest as shoulder portion 195. In some embodiments, aperture 305 is passed over the widening portion and is then constrained against the widened portion, potentially being held in place by friction forces. Alternatively, aperture 305 is passed over the widening portion a narrower portion being distal to the shoulder 195, and potentially the extension 254 is stabilized in place by overhanging an edge of aperture 305 over the widening portion, and/or shoulder 195.

In some embodiments, needle cap remover 100 serves as a peeler for cover 300, optionally at least its protective liner layer. For example, needle cap remover 100 is engaged with extension 254 through orifice 305. Optionally, user handle 190 which is optionally connected needle cap remover body 120, does not pull cover 300 directly away from the whole surface of the device base all at once (an act that might require a large force to overcome the sticking force over a large surface). In some embodiments, when handle 190 at is pulled, extension 254 pulls with it section 256 followed by section 250. In some embodiments, extension 304 guides the peeling initiation direction of section 250. In some embodiments, folded section 256 may unfurl, unfold, stretch and/or bend to allow a certain distance to build up. Optionally, unfolding of section 256 together with peeling of extension 304, converts the linear force away from housing 200 to a peeling force at the edge of adhesion of adhesive cover adhesive cover. The peeling force may optionally be along the surface of base of housing 200 and/or the peeling force may be directed away from the surface at an angle. For example, the angle of the peeling may range for example between 60-90 degrees and/or between 30-60 degrees and/or between 0 and 30 degrees.

Figure 3G:
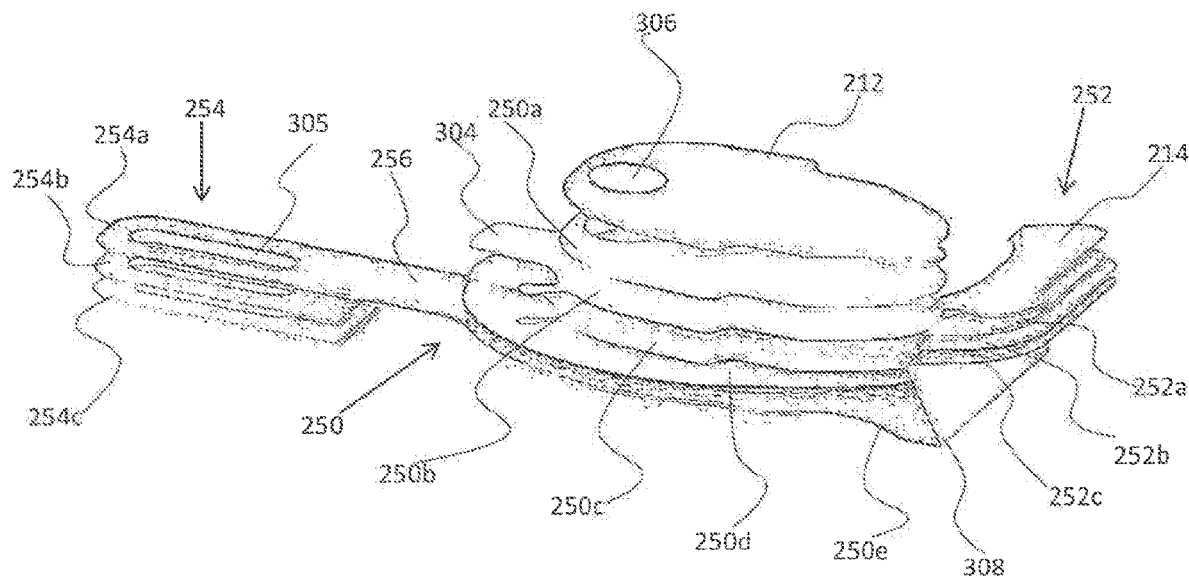

FIG. 3G illustrates details of possible structure of cover 300, having at least two active zones including an adhesive formed on a surface according to some embodiments of the current invention. In some embodiments a wall of a device (for example base of housing 200) may have an active surface (for example adhesive 250a and/or 250d). Optionally the adhesive may be formed in layers. For example, as illustrated in FIG. 3G, adhesive portion of cover 300 includes three layers. A first layer 250a includes a dual sided adhesive. Adhesive may for example, join a semi-stiff membrane 250b to the base 212. Membrane 250b may extend beyond the edges of the base, optionally extending in extension 304. Potentially, a semi-stiff extension beyond the edges of the base may in some embodiments make the injector adhere more strongly the skin of a user. In some embodiments, supporting membrane 250c is provided.

In some embodiments, the adhesive cover removal force ranges between 10-150 gr/cm. The adhesive cover removal force may be lower than the bending inertia of the adhesive membrane 250a. For example this may prevent bending of membrane 250b when removing the cover. An external face of membrane may optionally include an active surface. An active surface for the purpose of this application may be a surface that has active modality wherein the surface interacts with an external element facilitating the functioning of the device and an inactive modality wherein it substantially does not interact with the external element. For example, prior to enablement of the injector adhesive 250d may be inactive and/or protected by adhesive cover 250e.

Optionally, sections 250, 254 and/or 252 have different numbers of layers. In some embodiments, section 254 comprises adhesive layer 252a connecting base portion 214 to liner 252c and its supporting layer 252b. In some embodiments, extension 254 comprises extension of section 250 in the form of layer 254a, and further comprises adhesive layer 254b connecting to supporting layer 254c.

4 Exemplary Bifurcated Needle Cap Remover

Reference is now made to FIG. 4 illustrating various views of needle cap cover body 120, in accordance with some embodiments of the invention. In some embodiments, cover body 120 is provided as a cylinder having a bore 124. In some embodiments, a distal portion of body 120 is bifurcated. Optionally, at least two slits 101 provide the bifurcated portions, optionally creating at least two distinct portions.

In some embodiments, at least 4 slits 101 are provided such that at least 4 distinct portions are available at the distal end of body 120. Optionally, at least two of the portions comprise elastic portions 130. Alternatively or additionally, at least two of the portions comprise rigid portions 150. Optionally, at least two elastic portions 130 are positioned substantially diametrically to one another and/or optionally at least two rigid portions 150 are positioned substantially diametrically to one another.

In some embodiments, elastic portions 130 have a length extending beyond a top sill of a needle cap, for example, beyond 0.5 mm, 1 mm, or beyond 2 mm, or beyond 3 mm, or any length smaller, larger or intermediate. Optionally, elastic portions 130 extend in a range having length of about 3 mm to about 10 mm beyond the top rim of bore 124. In some embodiments, extended elastic portions comprise snaps 132, configured to overhang a top sill of needle cap 202. In some embodiments, snaps 132 comprise projections, optionally extending into an inner radial direction of bore 124. Optionally, the projections have a length of about 0.2 mm. Alternatively, the projections have a length of about 0.1 mm. the projections have a length of about 0.3 mm, or any length smaller, larger or intermediate to the mentioned lengths herein.

In some embodiments, intermediate slits 104, optionally not extending all the way to the distal rim of bore 124, are provided, optionally in elastic portions 130. Potentially, a configuration of positioning slits 101 and/or 104, and/or their size and/or shapes affect an elastic extent of elastic portions 130 and a rigidness extent of rigid portions 150. In some embodiments, the configuration and/or shape and/or size of slits 101 and/or 104 are configured to allow a small amount of force to push body 120 onto the needle cap and a large amount of force to pull body 120 away from the needle cap, optionally resulting in removal of the needle cap together with pulling of body 120. For example, a small amount of force is in the range of about 50 g to about 400 g. Alternatively, small force is in the range of about 100 g to about 300 g. Alternatively, small force is in the range of about 100 g to about 150 g. Optionally, a large amount of force is in the range of about 0.5-1.5 Kg. Alternatively, large amount of force is in the range of about 0.75 Kg to about 1.25 Kg. Alternatively, large amount of force is no more than 1 Kg.

In some embodiments, body 120 comprises at least one fastener 410, optionally having fastener lock 412 such as for example a projection, optionally located at the proximal portion of body 120. Potentially, fastener 410 is configured to snap and/or lock with complementary portions in connector body 170, potentially stabilizing body 120 in place. Alternatively or additionally, connector body 170 connects body 120 with handle 190. A potential advantage of providing multiple parts is to enable more degrees of freedom in an assembly process. In some embodiments, at least 3 fasteners 410 are provided, optionally equidistant from each other.

Reference is now made to FIGS. 4E and 4F, illustrating another embodiment of a needle cap remover, in accordance with some embodiments of the invention, and having at least four fasteners 410. FIG. 4E illustrates a front view of body cover 120 and FIG. 4F illustrates a front view of body 120 when connected to connector body 170 and while enveloping cap 202, which shields a needle connected to cannula 204 which is coupled to injector 206. Fasteners 410 are optionally coupled in their position to the position of the bifurcations. In some embodiments, fasteners 410 are provided in the rigid portions 150 of cover body 120. Optionally, cover body 120 comprises crack 430, possibly in the form of a non-straight line. A potential advantage of crack 430 is allowing more flexibility. A potential advantage of a non-straight form is allowing more stability.

Figure 4G:
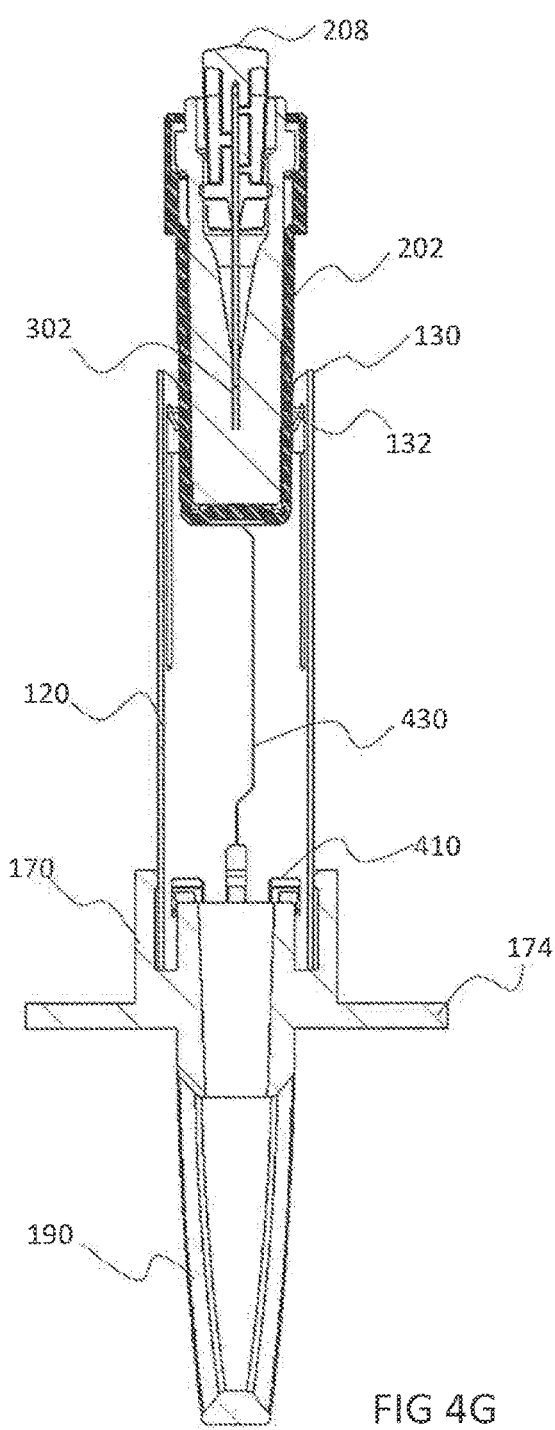
Figure 4H:
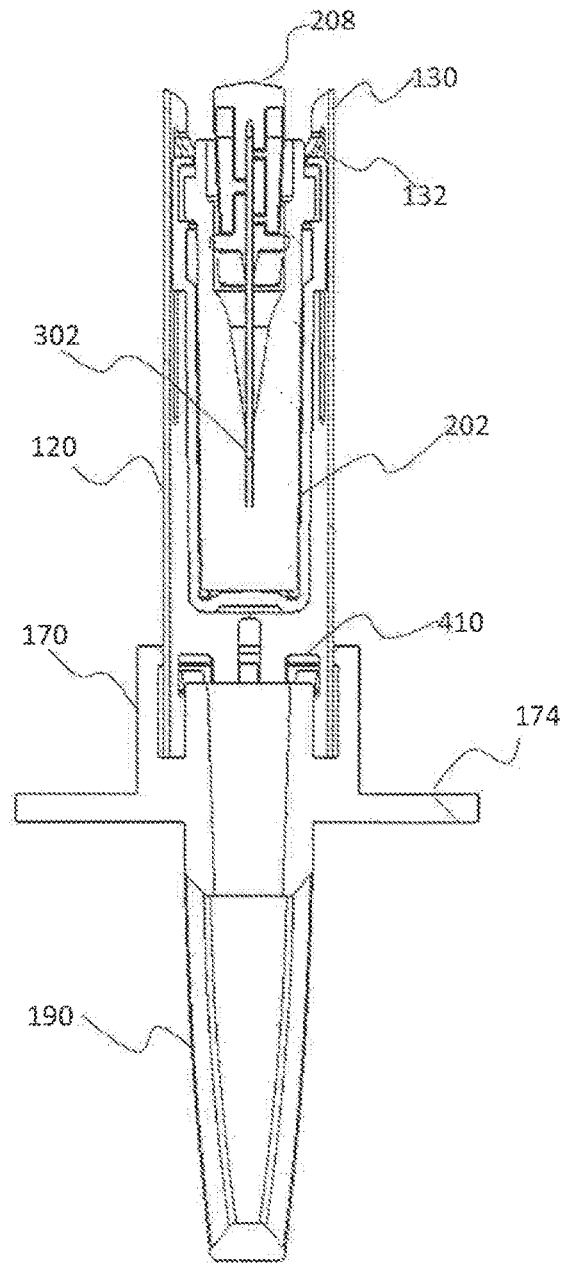

Reference is now made to FIGS. 4G and 4H, illustrating a cross section front view of the cap remover being pushed over the needle cap, in accordance with some embodiments of the invention, wherein FIG. 4G illustrates the needle cap remover being pushed mid-way along the needle cap and FIG. 4H illustrates the needle cap remover after snapping into place and having snaps 132 overhanging the top sill of the needle cap.

In some embodiments, the perimeter of the cap is not uniform, and it optionally includes a larger perimeter at its top end, i.e. the location where the needle projects outward from the syringe body. In some embodiments, hooks 132 are configured to define a perimeter which in its relaxed, unstressed state, can contains the perimeter of the bottom portion of cap 202, but cannot contain the perimeter of the top portion of cap 202. In some embodiments, the top portion of cap 202 comprises depressions for clasping hooks 132.

Figure 4I:
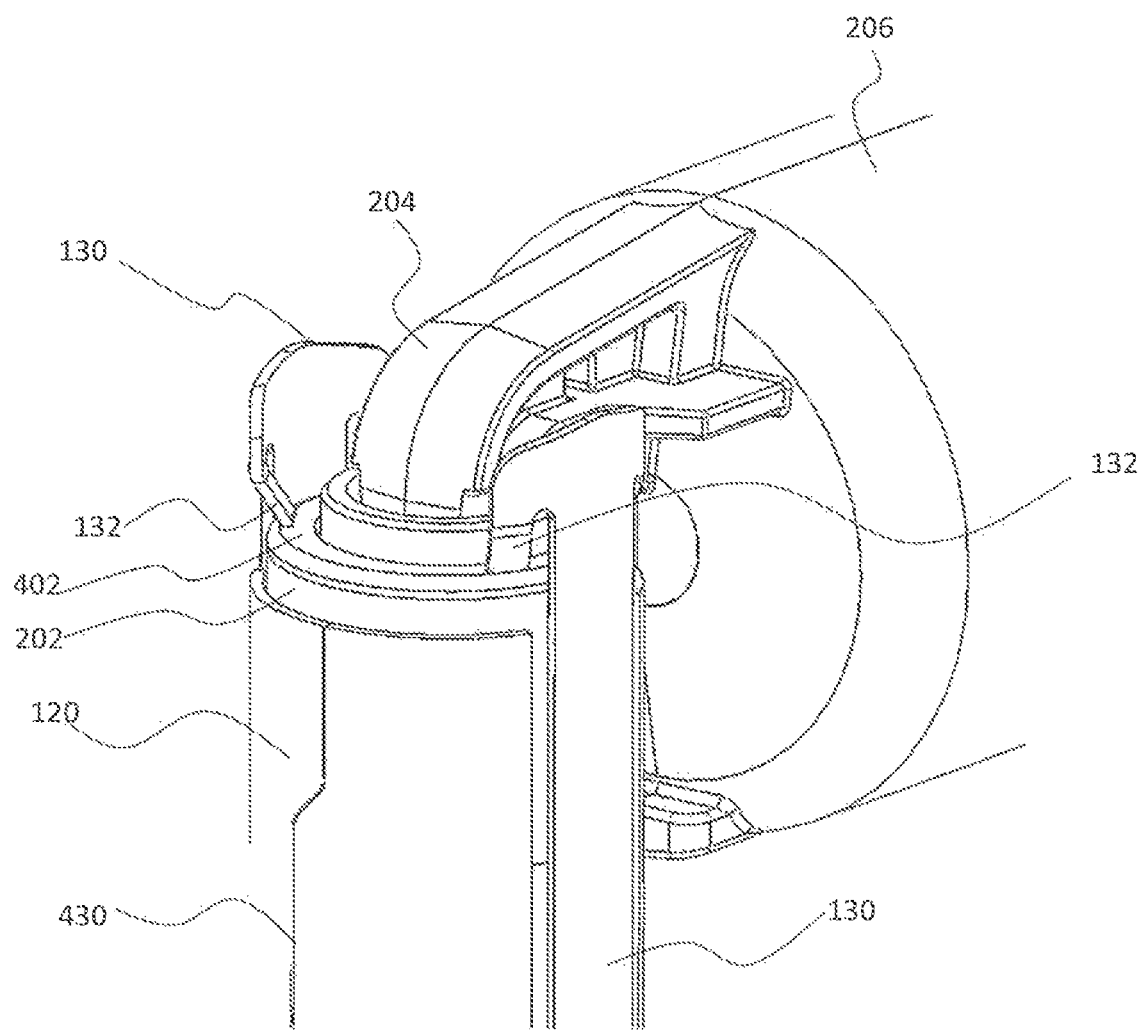
Figure 5A:
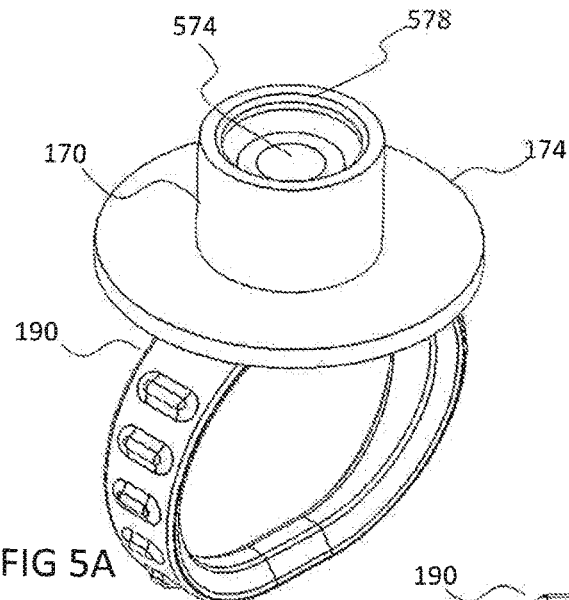
Figure 5B:
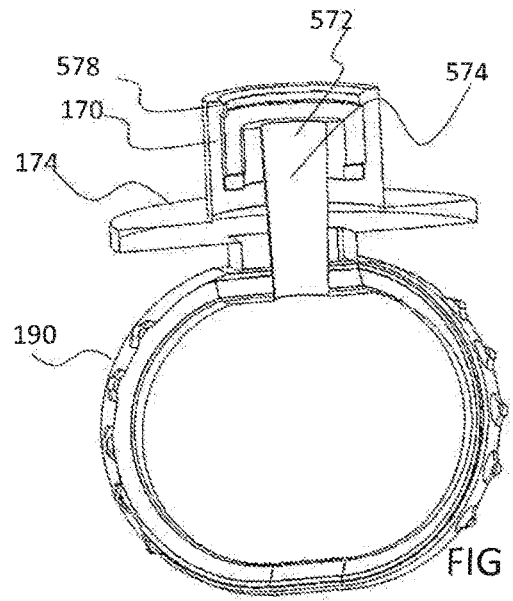
Figure 5C:
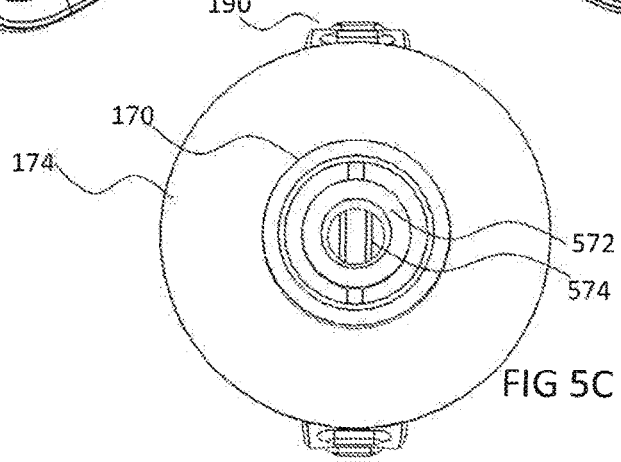
Figure 5D:
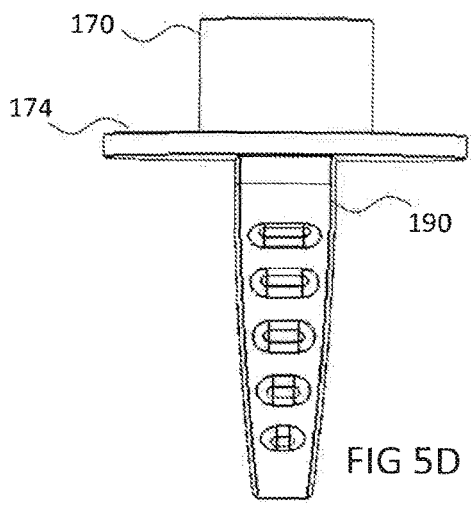
Figure 5E:
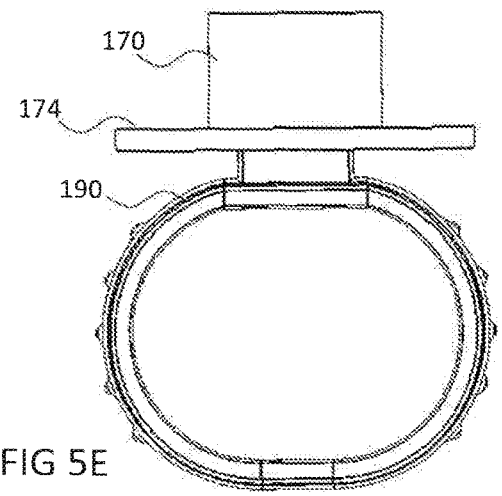

Reference is now made to FIG. 4I, illustrating a perspective partial view of cartridge 206, having a needle cap 202 protecting a needle connected to cannula 204, assembled with a cap remover device in accordance with some embodiments of the invention. In some embodiments, hooks 132 are configured to deflect elastic portions 130 away from the central axis of needle cap 202, optionally when passing by perimeters which are larger than defined by hooks 132. In some embodiments, hooks 132 are configured to overhang a top sill 402 of cap 202, optionally once the hooks pass the top portion of cap 202.

In some embodiments, hooks 132 include projections in a direction towards a central axis of the remover device. Optionally, the projections 132 are perpendicular to the longitudinal axis of the cover body 120. Alternatively, the projections are tilted towards the proximal portion of cover body 120. In some embodiments, the tilting of the projections 132 affects their resistance when pulling the cover body 120 with respect to cap 202. Optionally, a pulling force over cover body 120 causes projections 132 to increase their tilting angle with respect to the longitudinal axis of cover 120, potentially causing a mechanical interference resisting the pulling of cover body 120 without also pulling needle cap 202.

5 An Exemplary Connector for a Needle Cap Remover

Reference is now made to FIG. 5, illustrating a connector in the form of connector 170, in accordance with some embodiments of the current invention. In some embodiments, connector body 170 comprises a bore 574 sized and shaped to fit a needle cap remover cover body such as cover body 120, and/or to fit the needle cap proximal portion. In some embodiments, connector body 170 is provided with at least one complementary portion configured to lock connector body 170 onto cover body 120, optionally through fastener 410. In some embodiments, a connector undercut 578 is provided, enveloping at least a portion of connector bore 574 and optionally configured to clasp onto at least one fastener 410. In some embodiments, fastener 410 is shaped to allow easy insertion of connector body 170 in the direction towards the distal portion of cover body 120, but optionally clamp the connector 170 to the cover body 120 once undercut 578 has passed the fasteners position. In some embodiments, fasteners 410 are configured to prevent a lateral movement of the needle cap remover cover body with respect to the needle cap.

In some embodiments, handle 190 is connected to connector body 170, optionally through connector 572. Alternatively or additionally, handle 190 is made as a single unit together with connector body 170 and/or connector base 174.

6 Assembling a Needle Cap Remover onto a Needle Cap

Figure 6:
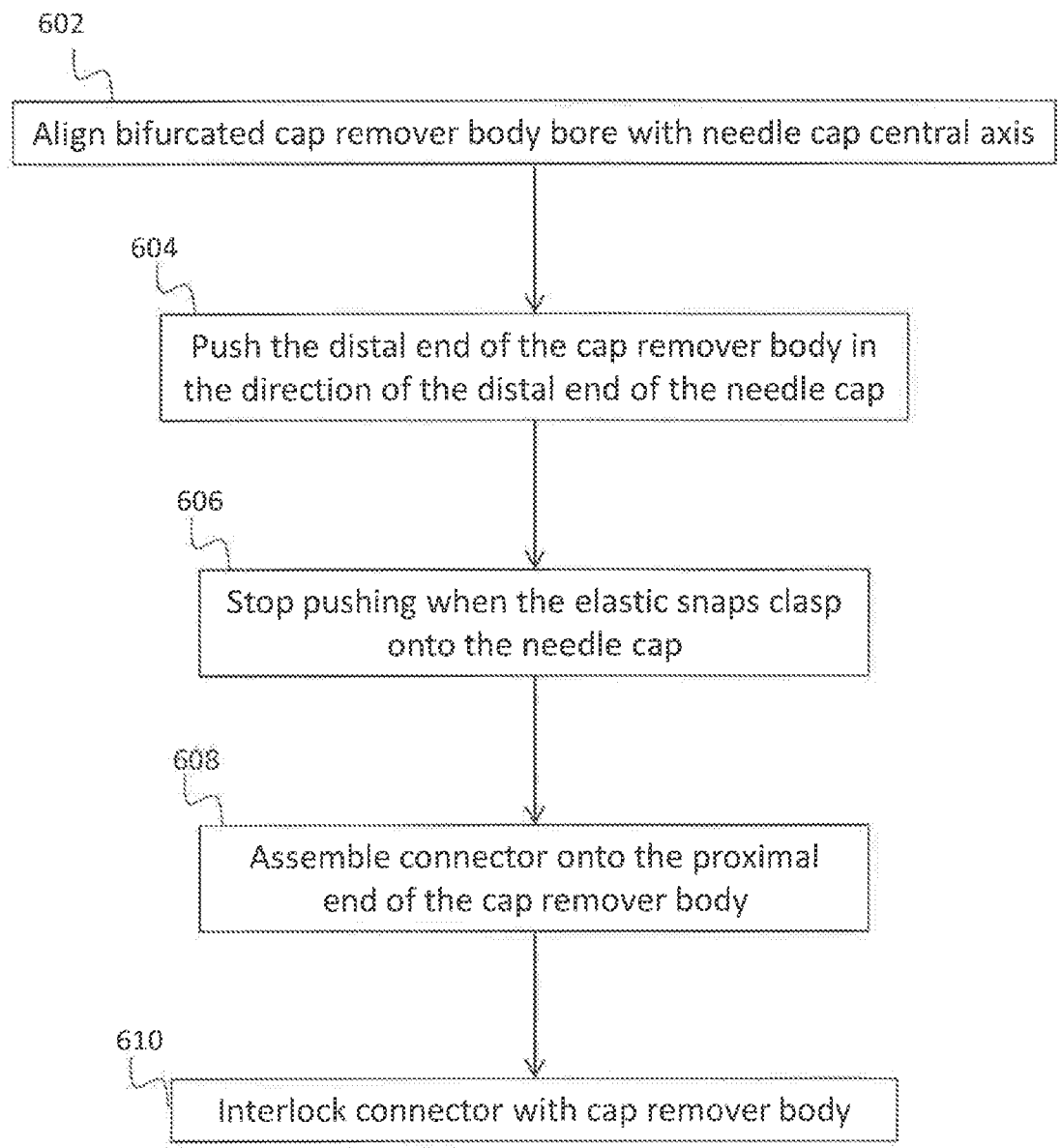
FIG. 6 is a flow chart illustrating an exemplary process for assembling a needle cap remover onto a needle cap, in accordance with some embodiments of the current invention.

Reference is now made to FIG. 6, having a flow chart illustrating an exemplary assembly of needle cap remover onto a needle cap, in accordance with some embodiments of the invention. In some embodiments, a cap remover body is aligned with a needle cap central axis 602. Alignment potentially prevents an excessive force exertion when pushing the remover onto the cap, which could lead to harming the needle, and/or disturbing the sterility of the inner zone of the needle cap.

In some embodiments, once the cap remover is substantially aligned with the needle cap, the cap remover is pushed towards the needle cap 604 optionally by inserting the proximal end of the needle cap into the distal end of the cap remover and pushing the distal end of the cap remover towards the direction of the distal end of the needle cap. Having bifurcations in the cap remover body potentially leads to elastic portions in the cap remover. In some embodiments, once the cover is pushed, the elastic portions, comprising snaps which optionally define a smaller circumference than the circumference of the needle cap, are pushed away from the central longitudinal axis of the cap remover.

In some embodiments, pushing of the cap remover stops when the elastic snaps reach beyond the top portion of the needle cap 606. In some embodiments, an interlocking mechanism prevents pushing of the cap remover beyond a certain point above the needle cap, such as for example, fasteners 410. Alternatively or additionally, the pushing of the cap remover stops when a sensor senses a reduction in the force resisting the push. In some embodiments, the snaps bounce into place thanks to the elastic properties of the elastic portions, optionally leading to the snaps overhanging a top sill of the needle cap.

Optionally, a connector, for example in the form of a clamp, is assembled onto the proximal end of the cap remover body 608. The connector potentially holds the cap remover body still with respect to the housing of an injector, and/or allow connection of the cap remover to additional features, such as a user handle and/or a liner covering operation features, for example adhesive portions and/or battery insulators.

In some embodiments, connector is pushed onto remover body until it interlocks in place 610, optionally by interlocking with at least one fastener 410 provided in the cap remover body.

Alternatively or additionally, the clamp, optionally already associated with a user handle, is interconnected to cap remover body prior to its enveloping onto the needle cap.

7 Assembling a Needle Cap Remover Having an Adhesive Liner, onto a Needle Cap

Figure 7:
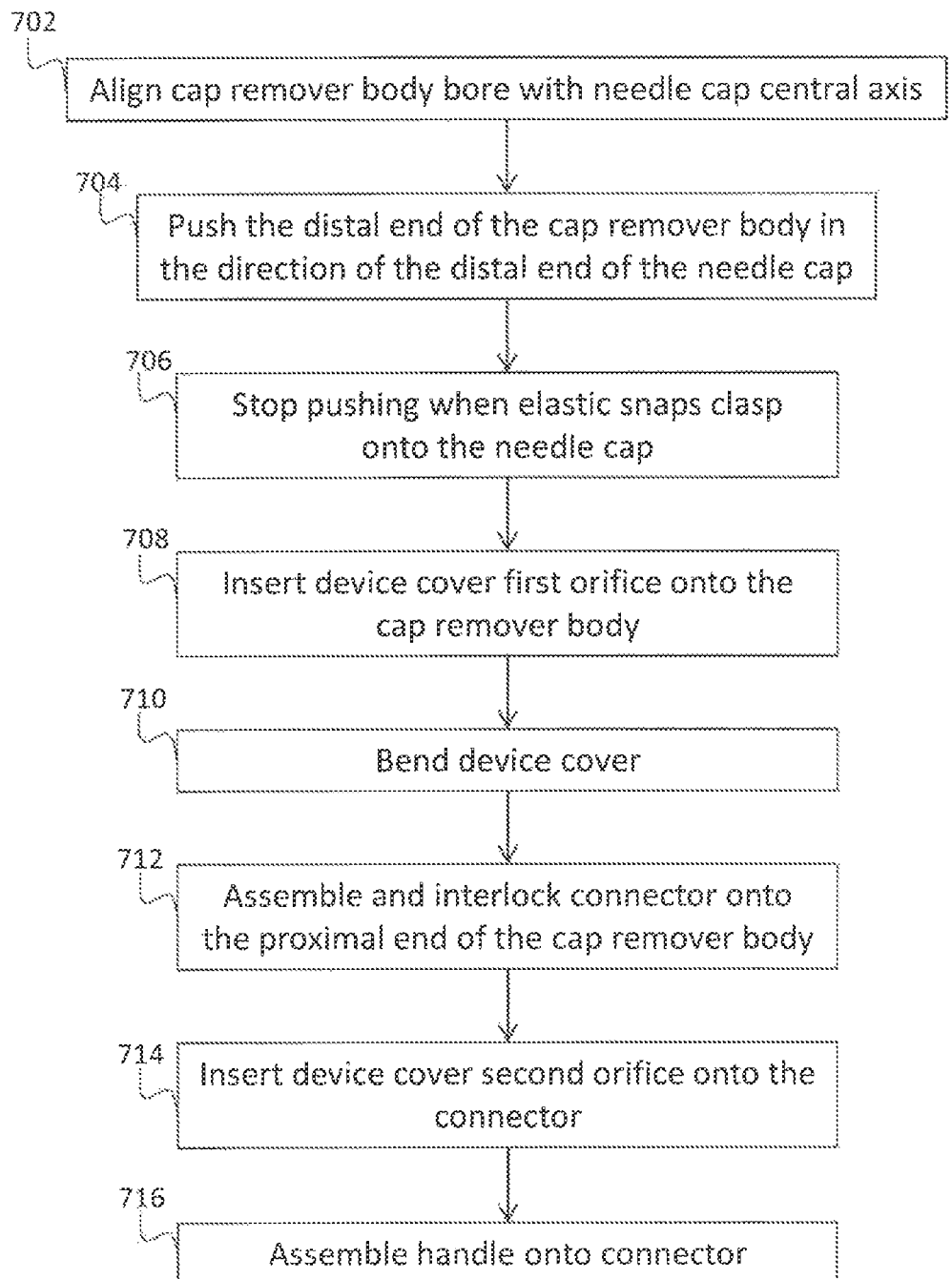
FIG. 7 is a flow chart illustrating an exemplary assembly of a needle cap remover assembly with an adhesive liner, in accordance with some embodiments of the current invention.

Reference is now made to FIG. 7, showing a flow chart illustrating an exemplary assembly process of a needle cap remover associated with a device cover, such as for example an adhesive liner, in accordance with some embodiments of the invention.

In some embodiments, aligning the central axis of the cap remover body with central axis of the needle cap 702 is done initially to prevent unnecessary force exertion. In some embodiments, the cap remover is then pushed onto the needle cap 704 as shown in 604, and optionally pushing is stopped when the body is clasped onto the cap 706, optionally by means of elastic snaps.

In some embodiments, the cap remover device is being inserted into a first orifice provided in a device cover 708, optionally comprising an adhesive liner. In some embodiments, a connector is assembled onto the cap remover 712, optionally securing the cover onto the cap remover.

In some embodiments, the device cover is bent 710, optionally at a portion which extends beyond the border of the injection system, and the connector body is inserted into a second orifice provided in the cover 714. Optionally, the second portion of the cover is secured after assembly of the user handle onto the connector 716.

8 Exemplary Assembly Process of an Automatic Needle Injector Device

Figure 8:
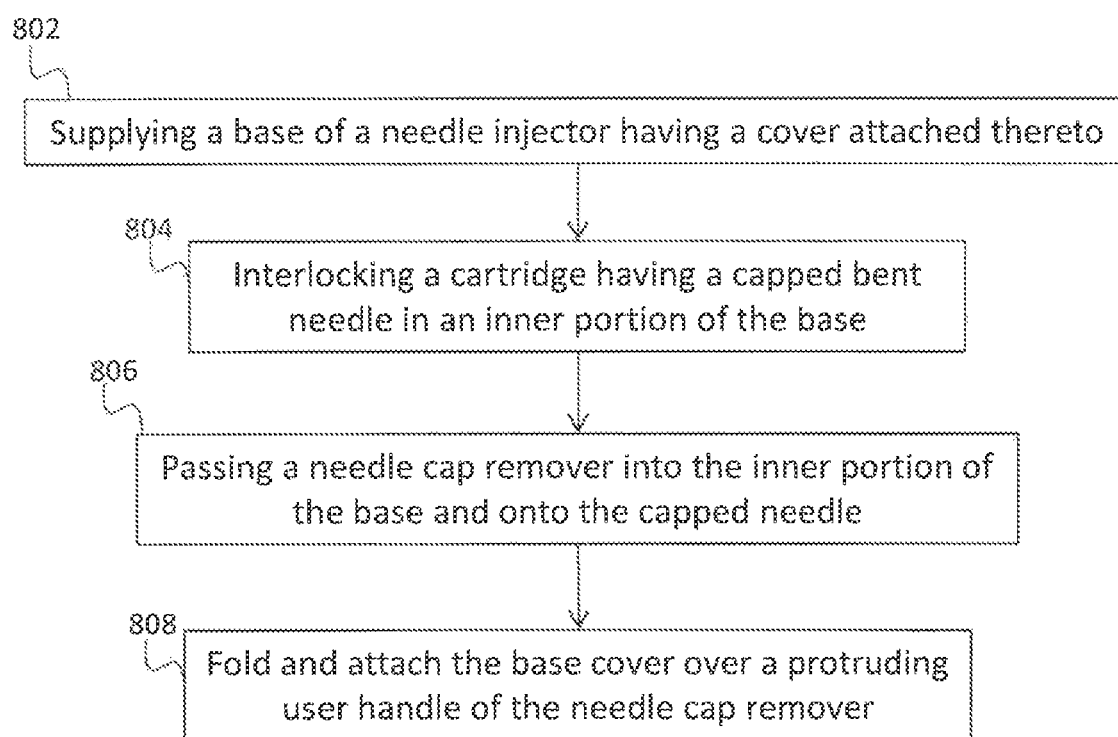
FIG. 8 is a flow chart illustrating an exemplary process assembling an automatic injector device, in accordance with some embodiments of the current invention.

Reference is now made to FIG. 8, illustrating an exemplary process of an assembly process of an automatic needle injector device, in accordance with some embodiments of the invention.

In some embodiments, a base of a needle injector housing is supplied 802, optionally being attached to a protective cover. In some embodiments, the protective cover comprises at least one adhesive layer, optionally for positioning and stabilizing the injector over a user's body. In some embodiments, the adhesive layer is protected by a second layer being a protective liner.

In some embodiments, a prefilled cartridge, optionally having a bend needle path, is positioned inside the base and interlocked to be engaged with it 804. Optionally, the cartridge is positioned such that a central axis of the cartridge to be parallel to the base-cover. In some embodiments, the cartridge comprises a capped bent needle. Optionally, the bent needle is centrally aligned with an orifice provided within the base, potentially allowing access from the outside of the injector housing, to the needle optionally residing within the injector housing. In some embodiments, the device cover covering the base also comprises a first aperture, optionally matching to the orifice of the base.

In some embodiments, a needle cap remover is passed from the outside portion of the base into the inside portion of the base, through the first aperture of the device cover 806. Optionally, the needle cap remover is pushed onto the capped needle. In some embodiments, the first aperture is sized and shaped to fit at least the circumference of the needle cap remover. In some embodiments, the needle cap remover is placed onto the capped needle in its distal end, optionally being in the inner portion of the injector. Optionally, the needle cap remover comprises in its proximal end a user handle, potentially being used to remover the needle cap remover with the needle cap.

In some embodiments, the needle cap remover is placed onto the capped needle while being attached to the user handle. Optionally, a cover edge which is not attached to the outer portion of the base, is folded over and attached to the user handle 808. In some embodiments, when pulling the user handle linearly, the cover edge is pulled with the handle and its connected needle cap remover, while the cover portion attached to the device is peeled from the direction of the edge.

In some embodiments, the user handle comprises a protruding member having a short dimension and a long dimension. Optionally, the cover is attached to the user handle by passing a second aperture of the cover over the protruding portion of the user handle. In some embodiments, the second aperture is assembled onto the user handle by orienting the second aperture of the cover to face the short dimension of the handle and rotating the cover onto the protruding element until the second aperture is oriented to face the long dimension.

9 Exemplary Multi-Part Cap Remover

In some embodiments, a cap remover is provided by having multiple parts. Optionally, the parts are assembled to a complete cap remover only while and/or after assembling onto the needle cap.

Figures 9A, 9B:
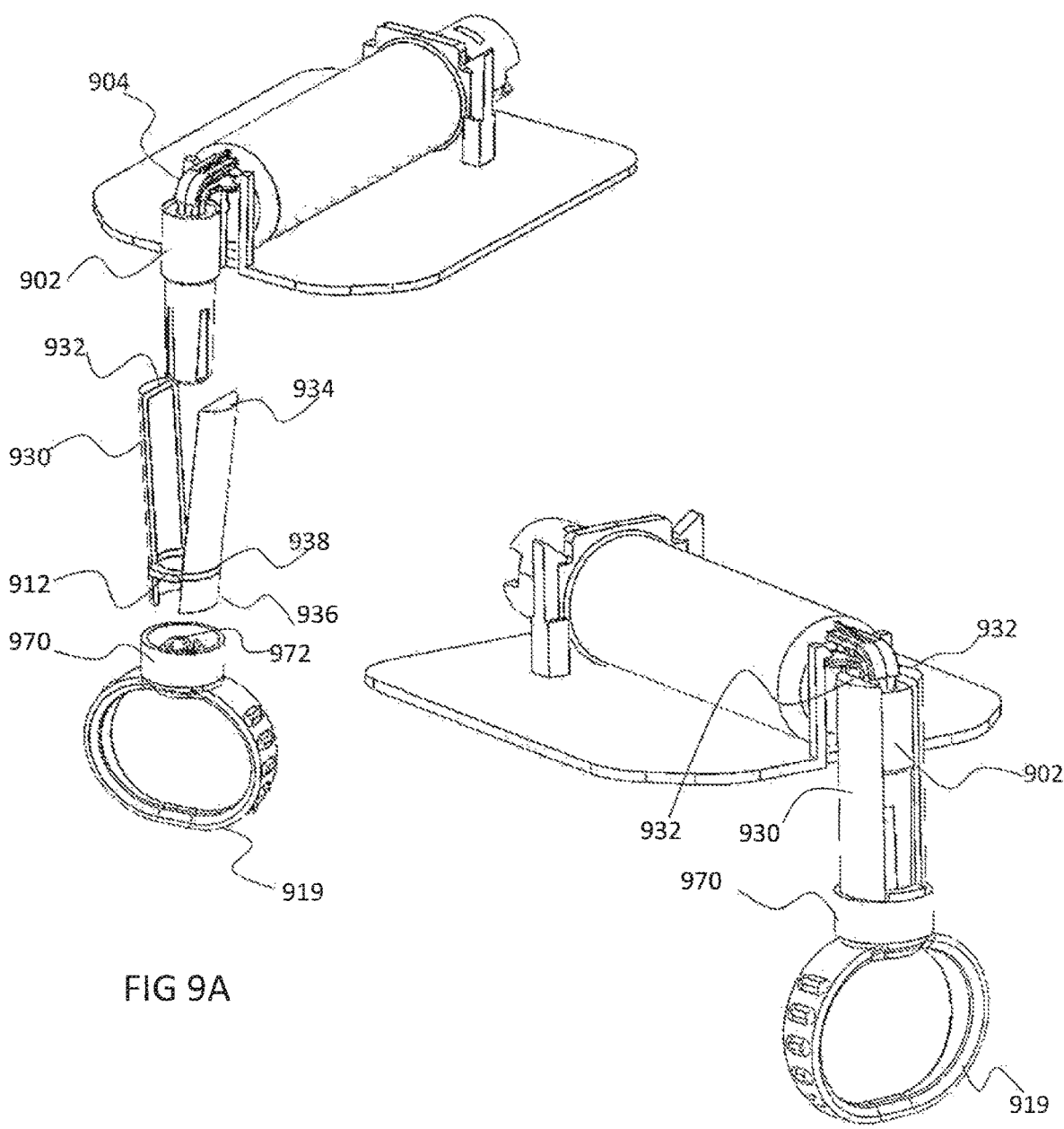
FIGS. 9A-B schematically illustrate an exemplary multipart cap remover, in accordance with some embodiments of the current invention, wherein FIG. 9A exemplifies a multipart cap remover in an open configuration and FIG. 9B exemplifies a multi-part cap remover in a tight configuration.

Reference is now made to FIGS. 9A-B, illustrating an exemplary embodiment of a multi part cap remover in accordance with some embodiments of the current invention. In some embodiments, a needle cap remover is provided having at least two elongated arms 930, sized and shaped to fit a longitudinal portion of a needle cap wall 902, optionally serving to protect cannula 904. Optionally, a distal portion 934 of the arms comprise enclosing members 932, optionally sized and shaped to fit a top surface of a needle cap. In some embodiments, a connector body 970 is sized and shaped to enclose over the at least two arms 930, optionally at their proximal portion 936, optionally leading to their clasping over the cap.

In some embodiments, an intermediate portion 938 of arm 930 comprises at least one fastening member; such as for example ring 912. Optionally, member 912 is configured to interlock with fastener 972 provided within connector body 970.

FIG. 9A illustrates an exemplary open configuration of the cap remover, having arms 930 tilted away from the longitudinal axis in their distal portion 934, optionally while being held together by ring 912. FIG. 9B illustrates an exemplary closed configuration, illustrating the enveloping of arms 930 around the needle cap, and their optional securing mechanism provided by connector 970, which optionally further comprises a user handle 919.

10 Assembling a Multi-Part Cap Remover onto a Needle Cap

Figure 10:
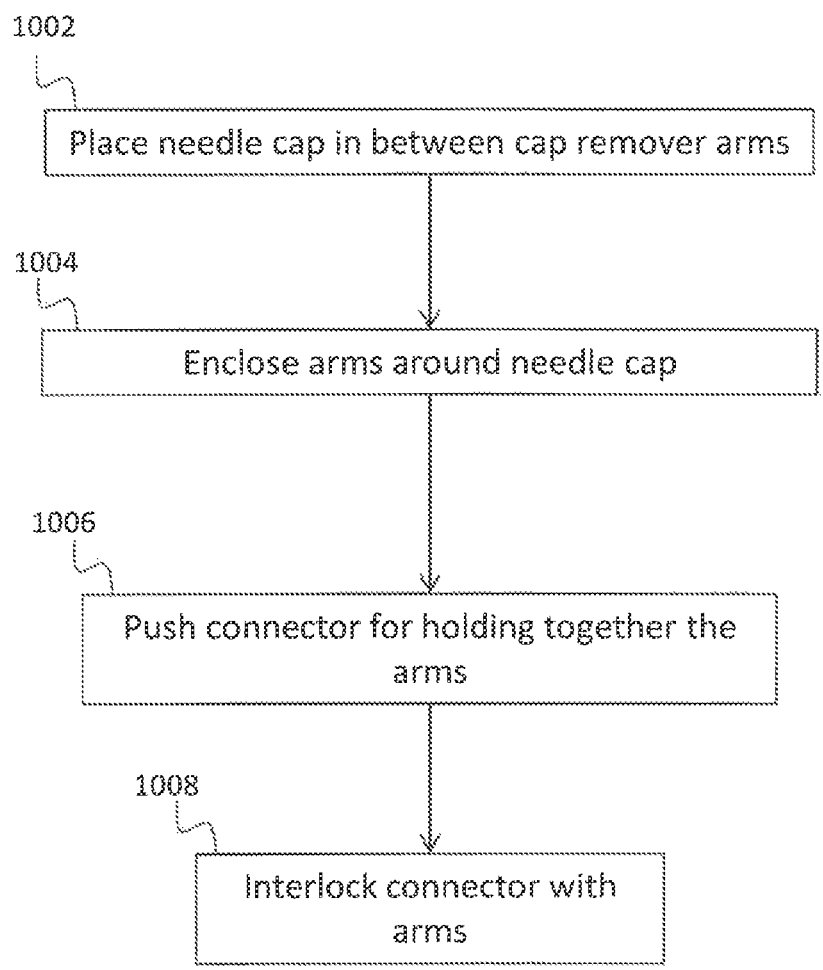
FIG. 10 is a flow chart illustrating a process of assembling a multi-part cap remover onto a needle cap, in accordance with some embodiments of the current invention.
Figures 11A, 11B:
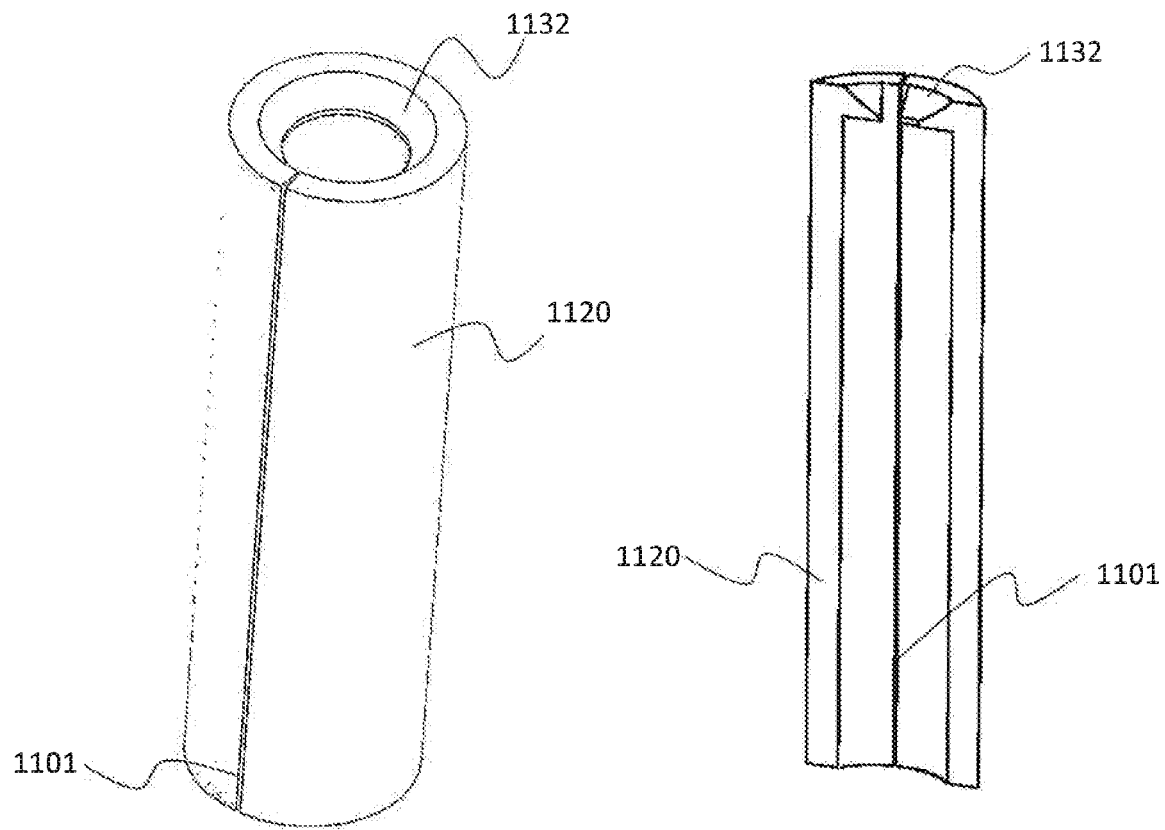
Figure 11C:
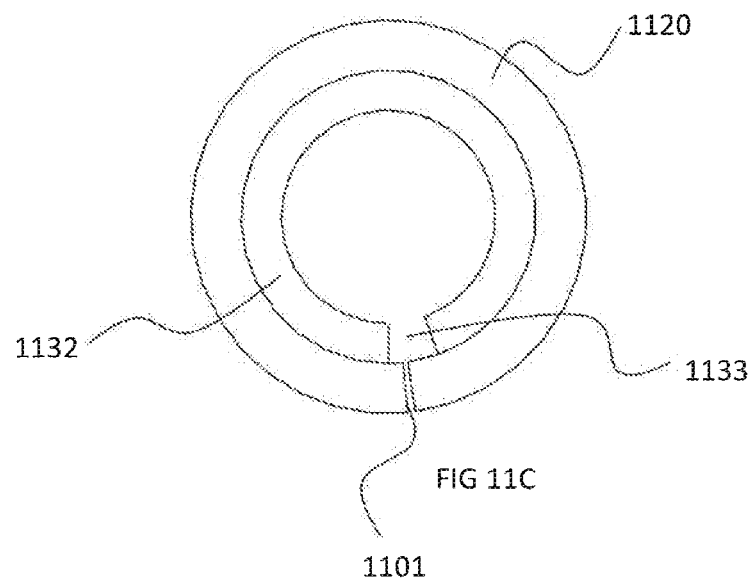

Reference is now made to FIG. 10, showing a flow chart illustrating an exemplary assembly process of a multi-part needle cap remover, in accordance with some embodiments of the current invention.

In some embodiments, a needle cap is placed in between the arms of a multi-part cap remover 1002. A potential advantage of having multiple parts is a flexibility in the perimeter defined by the arms. Optionally when the arms are open, they define a perimeter which is larger than the perimeter of the needle cap, potentially allowing their placement with a relatively low amount of force and/or low precision of aligning the central axis of the cap with the central axis of the cap remover.

Optionally, the arms enclose over the cap 1004 when a securing connector is pushed 1006 onto the proximal end of the arms, tilting them towards the needle cap. In some embodiments, the needle cap remover is held securely over the needle cap once the securing connector interlocks with the arms 1008 leading to securement of the arms over the needle cap. In some embodiments, the connector interlocks with the arms by clasping over the coupling element which mechanically couples the two arms, optionally the coupling element being a ring.

In some embodiments, no more than 25 g of force is exerted in order to interlock the connector with the arms, leading to their closed configuration. Alternatively, no more than 50 g force is exerted. Alternatively, no more than 100 g force is exerted. In some embodiments, in order to pull the needle cap no more than 0.5 Kg force is applied. Alternatively, no more than 0.7 Kg force is applied. Alternatively, no more than 0.9 Kg force is applied. Alternatively, no more than 1 Kg force is applied. Alternatively, no more than 1.2 Kg force is applied. Alternatively, no more than 1.5 Kg force is applied.

11 Exemplary of a Needle Cap Remover Having a Single Arm

In some embodiments, a cover body comprising a single arm 1120 is provided. Optionally, arm 1120 comprises a tubular shape. In some embodiments, slit 1101 is provided along the central longitudinal axis of arm 1120, optionally extending along the entire length of arm 1120. Potentially, slit 1101 provides elasticity to arm 1120, enabling the width of 1120 to open when force is exerted. In some embodiments, undercut 1132 is provided in at least a portion of the inner circumference of the top sill of arm 1120. Undercut 1132 is optionally sized and shaped to allow relatively easy insertion against a surface, together with relatively difficult removal, possibly due to its snap enablement. In some embodiments, aperture 1133 is provided to allow room for features comprised in the injector, which may hinder the space available for arm 1120.

As used herein the term "about" refers to ±25%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A cover for an injector having a needle, a needle cap, and a needle cap remover having a coupler for the needle cap and a user handle, said user handle having a protruding element opposite said coupler, said cover comprising:
   at least one adhesive layer configured to cover a surface of the injector;
   at least one liner layer covering said adhesive layer;
   an extension configured to extend beyond said surface of the injector;
   a first aperture through said adhesive layer and said at least one liner layer, the first aperture being configured to be aligned with an opening in said surface of the injector, said first aperture being configured for passage of said coupler;
   a second aperture through said extension, the second aperture being elongated; and
   a rigid layer surrounding at least a portion of said second aperture.

2. The cover of claim 1, wherein the extension and the at least one liner layer are made of a single integral piece of material.

3. The cover of claim 1, further comprising at least one intermittent supporting layer attached to said at least one liner layer, said at least one intermittent supporting layer being discontinuous over an area of said cover.

4. A method of assembling an automatic injector device having an interior volume and a base located between said interior volume and an exterior surface defined by said base, said base having an opening, said method comprising:
   supplying the cover of claim 1;
   passing a distal portion of the needle cap remover through said first aperture and said opening in the base;
   coupling said distal portion to the needle cap positioned in said interior volume;
   bending said extension over a protruding element provided in a proximal end of said needle cap remover, said protruding element having a long dimension and a short dimension;
   orienting said second aperture of said cover to face said short dimension of said protruding element; and
   rotating said cover onto said protruding element until said second aperture is oriented to face said long dimension.

5. The method of claim 4, further comprising interlocking a cartridge having a capped needle in an inner portion of said base, a central axis of the needle cap being perpendicular to said cover and said capped needle centrally aligned with said first aperture of said cover and said opening of said base.

6. The method of claim 4, wherein said cover converts a linear movement of the needle cap remover away from the exterior surface into a peeling force on said cover.

7. The method of claim 4, further comprising sliding said second aperture along said long dimension in an offset direction from a central axis of said long dimension.

8. The method of claim 4, further comprising stabilizing said extension of said cover onto said protruding element by constraining said second aperture against a widening portion of said protruding element.

9. The method of claim 8, wherein said constraining further includes passing said second aperture over said widening portion into a narrower portion and overhanging an edge of said second aperture over said widening portion.

10. The cover of claim 1, wherein the protruding element has a short dimension and a long dimension, and the second aperture is configured to slide along the long dimension of the user handle.

11. The cover of claim 1, wherein the first aperture is circular.

12. The cover of claim 1, wherein the second aperture has a pair of straight sides and a pair of rounded ends.

13. The cover of claim 1, wherein said extension comprises a resilient material configured to stretch the second aperture over a shoulder of the user handle and to overhang a top sill of said shoulder.

14. The cover of claim 13, wherein said resilient material is disposed in said second aperture.

15. A cover for an injector having a needle, a needle cap, and a needle cap remover having a coupler for the needle cap and a user handle, the cover comprising:
- at least one adhesive layer configured to cover a surface of the injector;
- at least one liner layer covering the adhesive layer;
- an extension configured to extend beyond the surface of the injector;
- a first aperture through the adhesive layer and the at least one liner layer, the first aperture being configured to be aligned with an opening in the surface of the injector, the first aperture being configured for passage of the coupler; and
- a second aperture through the extension, the second aperture being elongated.

16. The cover of claim 15, further comprising a rigid layer surrounding at least a portion of the second aperture.

17. The cover of claim 15, wherein the extension comprises a resilient material configured to stretch the second aperture over a shoulder of the user handle and to overhang a top sill of the shoulder.

18. The cover of claim 15, wherein the extension and the at least one liner layer are made of a single integral piece of material.

19. The cover of claim 15, further comprising at least one intermittent supporting layer attached to said at least one liner layer, said at least one intermittent supporting layer being discontinuous over an area of said cover.

20. The cover of claim 15, wherein the first aperture is circular, and the second aperture has a pair of straight sides and a pair of rounded ends.

21. A system comprising:
- an injector having a needle;
- a needle cap;
- a needle cap remover having a coupler for the needle cap and a user handle, the user handle having a protruding element opposite the coupler, the protruding element having a short dimension and a long dimension; and
- a cover including:
  - at least one adhesive layer covering a surface of the injector,
  - at least one liner layer covering the adhesive layer,
  - an extension extending beyond the surface of the injector,
  - a first aperture through the adhesive layer and the at least one liner layer, the first aperture being aligned with an opening in the surface of the injector, and the first aperture being configured for passage of the coupler, and
  - a second aperture through the extension, wherein the second aperture is elongated and has a length that is longer than the short dimension.

22. The system of claim 21, wherein the cover comprises a rigid layer surrounding at least a portion of the second aperture.

23. The system of claim 21, wherein the extension and the at least one liner layer are made of a single integral piece of material.

24. The system of claim 21, wherein the length of the second aperture is shorter than the long dimension of the protruding element.

25. The system of claim 21, wherein the extension comprises a resilient material configured to stretch the second aperture over a shoulder of the user handle and to overhang a top sill of the shoulder.

26. The system of claim 21, wherein the first aperture is circular, and the second aperture has a pair of straight sides and a pair of rounded ends.

* * * * *